United States Patent
Kaye et al.

(10) Patent No.: US 10,417,380 B1
(45) Date of Patent: Sep. 17, 2019

(54) SYSTEMS AND METHODS FOR DETERMINING AND COMMUNICATING A PRESCRIPTION BENEFIT COVERAGE DENIAL TO A PRESCRIBER

(71) Applicant: McKesson Corporation, San Francisco, CA (US)

(72) Inventors: Elizabeth S. Kaye, Suwanee, GA (US); Stacy Hopkins, Loganville, GA (US); Roger G. Pinsonneault, Alpharetta, GA (US)

(73) Assignee: MCKESSON CORPORATION, San Francisco, CA (US)

( * ) Notice: Subject to any disclaimer, the term of this patent is extended or adjusted under 35 U.S.C. 154(b) by 415 days.

(21) Appl. No.: 15/137,371

(22) Filed: Apr. 25, 2016

Related U.S. Application Data

(63) Continuation-in-part of application No. 14/145,027, filed on Dec. 31, 2013.

(51) Int. Cl.
*G06Q 40/08* (2012.01)
*G06Q 50/22* (2018.01)
*G06F 19/00* (2018.01)

(52) U.S. Cl.
CPC ........ *G06F 19/328* (2013.01); *G06F 19/3456* (2013.01); *G06Q 40/08* (2013.01); *G06Q 50/22* (2013.01)

(58) Field of Classification Search
CPC ..... G06Q 40/08; G06Q 10/0635; G06Q 50/22
(Continued)

(56) References Cited

U.S. PATENT DOCUMENTS

| 5,628,530 A | 5/1997 | Thornton |
| 6,012,035 A | 1/2000 | Freeman et al. |

(Continued)

FOREIGN PATENT DOCUMENTS

| CA | 2482370 | 3/2006 |
| WO | WO 1995003569 | 2/1995 |

(Continued)

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

(Continued)

*Primary Examiner* — Hai Tran
(74) *Attorney, Agent, or Firm* — Alston & Bird LLP

(57) ABSTRACT

Systems and methods are provided for determining and communicating prescription benefit coverage information to a prescriber of the product, service, or medication. A prescription benefit check request may be received by the service provider computer from a healthcare provider computer for the prescriber of the product, service, or medication. The service provider computer may format a prescription request for the prescribed product, service, or medication and transmit the prescription request to a pharmacy claims processor computer for processing. The service provider computer may receive a prescription response that includes a determination of the prescription request from the pharmacy claims processor computer. The service provider computer may determine that the prescription request was denied and the basis for the denial from the prescription response and can transmit a prescription benefit check (Continued)

response that includes at least a portion of the data in the prescription response to the healthcare provider computer.

20 Claims, 17 Drawing Sheets

(58) Field of Classification Search
USPC .......................................................... 705/4
See application file for complete search history.

(56) References Cited

U.S. PATENT DOCUMENTS

| | | |
|---|---|---|
| 6,757,898 B1 | 6/2004 | Llsen et al. |
| 6,769,228 B1 | 8/2004 | Mahar |
| 7,155,397 B2 | 12/2006 | Alexander et al. |
| 8,036,913 B1* | 10/2011 | Pinsonneault ........ G06F 19/328 |
| | | 705/2 |
| 8,036,914 B1 | 10/2011 | Pinsonneault |
| 2001/0029483 A1 | 10/2001 | Schultz et al. |
| 2001/0056359 A1 | 12/2001 | Abreu |
| 2002/0002495 A1 | 1/2002 | Ullman |
| 2002/0032582 A1 | 3/2002 | Feeney et al. |
| 2002/0087583 A1 | 7/2002 | Morgan et al. |
| 2002/0111832 A1 | 8/2002 | Judge |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0149625 A1 | 8/2003 | Leonardi et al. |
| 2003/0154163 A1 | 8/2003 | Phillips et al. |
| 2003/0187690 A1 | 10/2003 | Miller |
| 2003/0229540 A1 | 12/2003 | Algiene |
| 2004/0039599 A1 | 2/2004 | Fralic |
| 2004/0059607 A1* | 3/2004 | Ball ...................... G06F 19/326 |
| | | 705/3 |
| 2004/0073457 A1 | 4/2004 | Kalies |
| 2004/0078234 A1 | 4/2004 | Tallal, Jr. |
| 2004/0117323 A1 | 6/2004 | Mindala |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0149784 A1 | 7/2006 | Tholl et al. |
| 2006/0184391 A1 | 8/2006 | Barre et al. |
| 2006/0224417 A1 | 10/2006 | Werner |
| 2006/0259363 A1 | 11/2006 | Jhetam |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0103836 A1* | 5/2008 | Park ...................... G06F 19/328 |
| | | 705/4 |
| 2008/0262948 A1 | 10/2008 | Grady et al. |
| 2010/0030667 A1 | 2/2010 | Chudy et al. |
| 2010/0145730 A1 | 6/2010 | Abreu |
| 2011/0161109 A1* | 6/2011 | Pinsonneault ......... G06Q 50/22 |
| | | 705/3 |

FOREIGN PATENT DOCUMENTS

| | | |
|---|---|---|
| WO | WO 2000039737 | 7/2000 |
| WO | WO 2007025295 | 3/2007 |

OTHER PUBLICATIONS

Anonymous, Medic; On-line Goes In-House, Chain Store Age Executive, Jan. 1987, vol. 63, Issue 1, USA; only.
Anonymous, Pharmacy Industry Leaders Launch Firm to Supply Real-Time Data. PR Newswire. Jul. 30, 2001, p. 1, York, NY, USA.
Anonymous, TechRx Announces Successful Beta Deployment of T-Rex. PR Newswire. May 13, 2002.
Final Office Action for U.S. Appl. No. 13/827,676 dated Jul. 13, 2015.
Final Office Action for U.S. Appl. No. 14/145,027 dated Nov. 19, 2015.
Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.
Non-Final Office Action for U.S. Appl. No. 12/388,956 dated Feb. 3, 2011.
Non-Final Office Action for U.S. Appl. No. 13/827,676 dated Dec. 26, 2014.
Non-final Office Action for U.S. Appl. No. 13/827,676 dated Dec. 30, 2015.
Non-Final Office Action for U.S. Appl. No. 14/145,027 dated Mar. 23, 2015.
Notice of Allowance for U.S. Appl. No. 12/388,956 dated Jun. 14, 2011.
Sampson, R.J., Taking Control of Health Care Costs, Best's Review—Life Health Insurance Edition, Nov. 1983, 84, Issue 7, USA; Abstract only.

* cited by examiner

SYSTEMS AND METHODS FOR DETERMINING AND COMMUNICATING A PRESCRIPTION BENEFIT COVERAGE DENIAL TO A PRESCRIBER

CROSS-REFERENCE TO RELATED APPLICATIONS

This application is a continuation-in-part of and claims priority under 35 U.S.C. § 120 to co-pending U.S. patent application Ser. No. 14/145,027, titled Systems and Methods for Determining and Communicating Patient Copay Information to a Prescriber, which was filed on Dec. 31, 2013, the entire contents of which is hereby incorporated herein by reference for all purposes.

TECHNICAL FIELD

Aspects of the disclosure relate generally to determining and communicating benefit coverage details for a product to be prescribed to a patient to the prescriber of the product at the time of prescribing and more particularly, to systems and methods for determining and communicating a prescription benefit coverage denial to the prescriber during a prescription process.

BACKGROUND

Providing prescribers, at the time they are prescribing a product (e.g., medication, product, or service) to a patient, accurate information as to why the benefits coverage request for the product an patient will be denied by a pharmacy claims processor (e.g., pharmacy benefits manager (PBM), an insurance company, a government payor affiliated entity, another third-party payor) can be a challenge with today's healthcare provider systems. Over time, the financial structures and rules for providing prescription benefits to patients have grown increasingly more sophisticated (i.e. formulary tiers, deductibles, maximum benefits, coverage limits, prior authorization requirements, plan limitations, etc.). Today, prescribers attempt to determine if the patient has coverage and the amount that a patient may have to pay out-of-pocket, patient pay, for a proposed prescription product by establishing patient eligibility, including association to a specific formulary, downloading formulary information in the healthcare provider device, comparing a proposed medication to the formulary to determine alignment, or writing the prescription and waiting to see if they pharmacy calls with a request for an alternative medication. However, these solutions are inadequate for reasons such as they do not reflect whether the patient will actually have prescription benefit coverage for the prescribed product (based on the numerous rules and factors) or the patient's actual out-of-pocket spend. For example, formulary information may not be current and does not reflect the benefit limit and the patient's position with regard to those limits or whether a patient has an approved prior authorization on file.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Figure 1A:
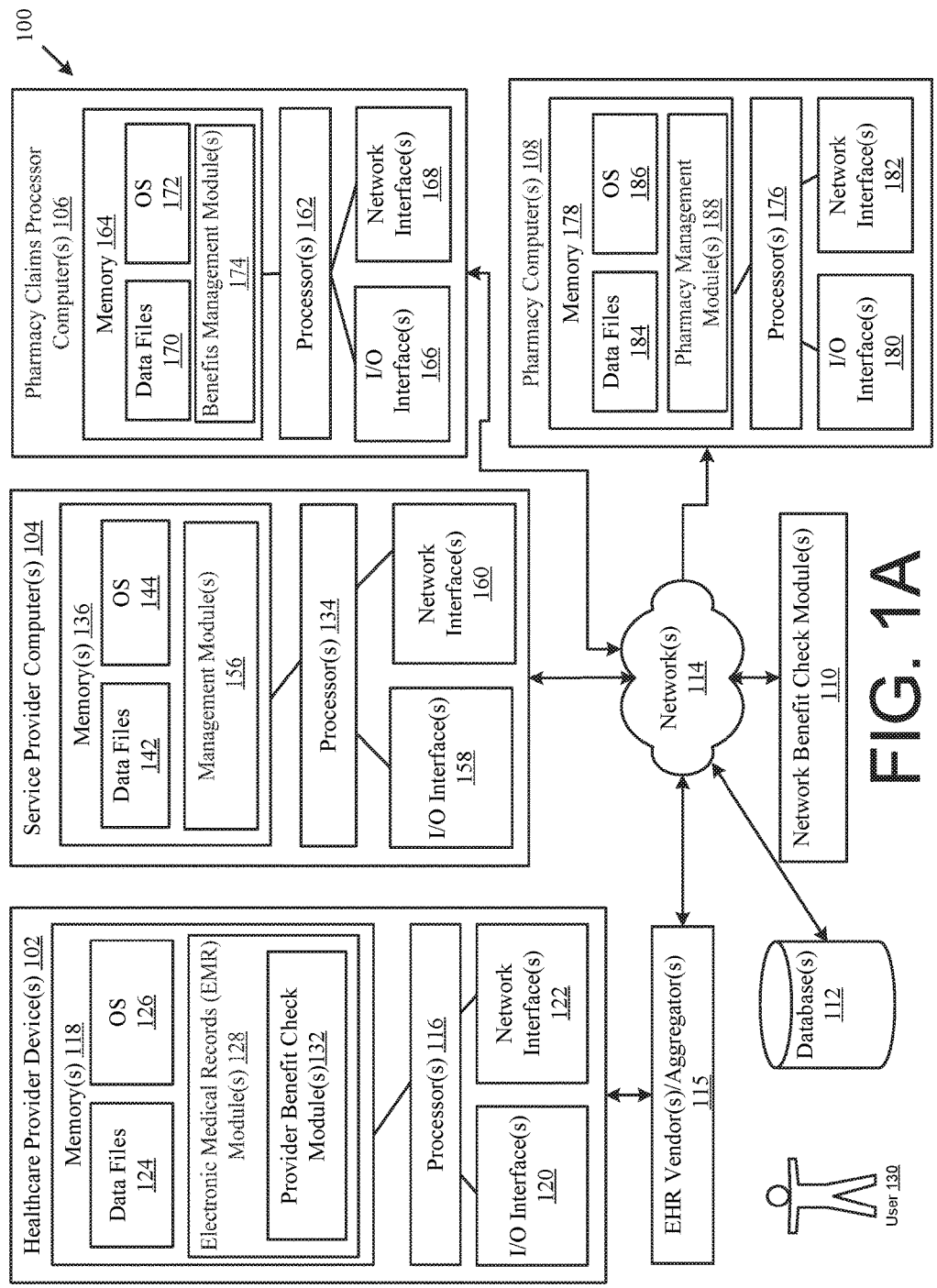
FIGS. 1A and 1B illustrate an example system for facilitating, among other things, determining and communicating accurate patient pay or prescription benefit coverage denial information to the prescriber during a prescription process, according to one exemplary embodiment.

Exemplary embodiments will now be described more fully hereinafter with reference to the accompanying drawings, in which example embodiments are shown. The concepts disclosed herein may, however, be embodied in many different forms and should not be construed as limited to the example embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods for determining and communicating patient pay information or prescription benefit coverage denial information to the prescriber while the prescriber is determining which medication to prescribe to the patient during the prescribing process. In some example implementations, a prescription benefit check request may be communicated (either directly or indirectly via an EHR vendor/aggregator system) from a healthcare provider computer associated with a healthcare provider (e.g., a prescriber (e.g., a doctor, dentist, nurse, nurse practitioner, hospital, or clinic) of products, services, or medications) and received by a service provider computer. In one example, the prescription benefit check request may include pharmacy benefit information captured by a healthcare provider during a patient visit. For example, the healthcare provider may capture the patient's name, date of birth, gender, preferred pharmacy identification, and benefits provider identification (e.g., pharmacy benefits manager, healthcare or pharmacy benefits insurance provider, government healthcare insurance provider, etc.). Additionally, the prescription benefit check request may include one or more identifications of the medication to be prescribed to the patient. In some examples, the prescription benefit check request may be communicated in real-time or near real-time to the service provider computer. The service provider computer may determine a request type of the prescription benefit check request. In some implementations, the request type may include, without limitation, a pharmacy request (e.g., a pharmacy billing request (e.g., request type "B1"), a billing request (e.g., request type "P1"), or a predetermination of benefits request (e.g., request type "D1")) formatted under an NCPDP Telecom standard. Additionally, the service provider computer may determine one or more destination identifiers or patient pharmacy benefit provider identifiers in the prescription benefit check request. For example, the processing of the prescription benefit check request may include, without limitation, a determination of (i) whether the included pharmacy identification associated with the patient's preferred pharmacy is a contracted pharmacy; (ii) whether all of the required patient and/or prescriber information is included in the prescription benefit check request; and/or (iii) whether the benefits provider identification included in the prescription benefit check request is an identification for a supported benefits provider. The service provider computer may also access pharmacy information captured in a previously submitted prescription request determined to meet one or more predetermined pharmacy and medication qualifiers.

The service provider computer may generate a prescription request based on the request type identified in the prescription benefit check request, insert all or a portion of the data from the prescription benefit check request into the prescription request and communicate the prescription request to the determined benefits provider (e.g., a pharmacy claims processor computer for the determined benefits provider) as a particular form of prescription request. The benefits provider may process the prescription request and communicate a prescription response to the service provider computer. The prescription response may include a status indicator to indicate whether the prescription request is approved or denied. An approved response can also data indicating the patient pay amount in one or more fields of the response while a denied response can include a denial reason. In addition, in either the approved response or the denied response the response can also include additional messaging, which can be from a variety of stakeholders. Upon receipt of the prescription response, the service provider computer may capture predetermined portions of the prescription response, generate a prescription benefit check response, insert portions of the prescription response into the prescription benefit check response and electronically transmit the prescription benefit check response either directly or indirectly via the EHR vendor/aggregator system to the healthcare provider computer. In situations where the prescription response indicates that the prescription request is approved, the service provider may generate a reversal request of corresponding request type and communicate it the benefits provider following a suitable predetermined waiting period. For example, the suitable time interval may include, but is not limited to, 30 seconds, 2 minutes, 5 minutes, or the like. The benefits provider may process the reversal request and communicate a reversal response to the service provider computer. The service provider computer may employ various methods and multiple attempts to ensure the reversal request is processed by the benefits provider. Additionally, the service provider may capture pharmacy specific information.

System Overview

Figure 1B:
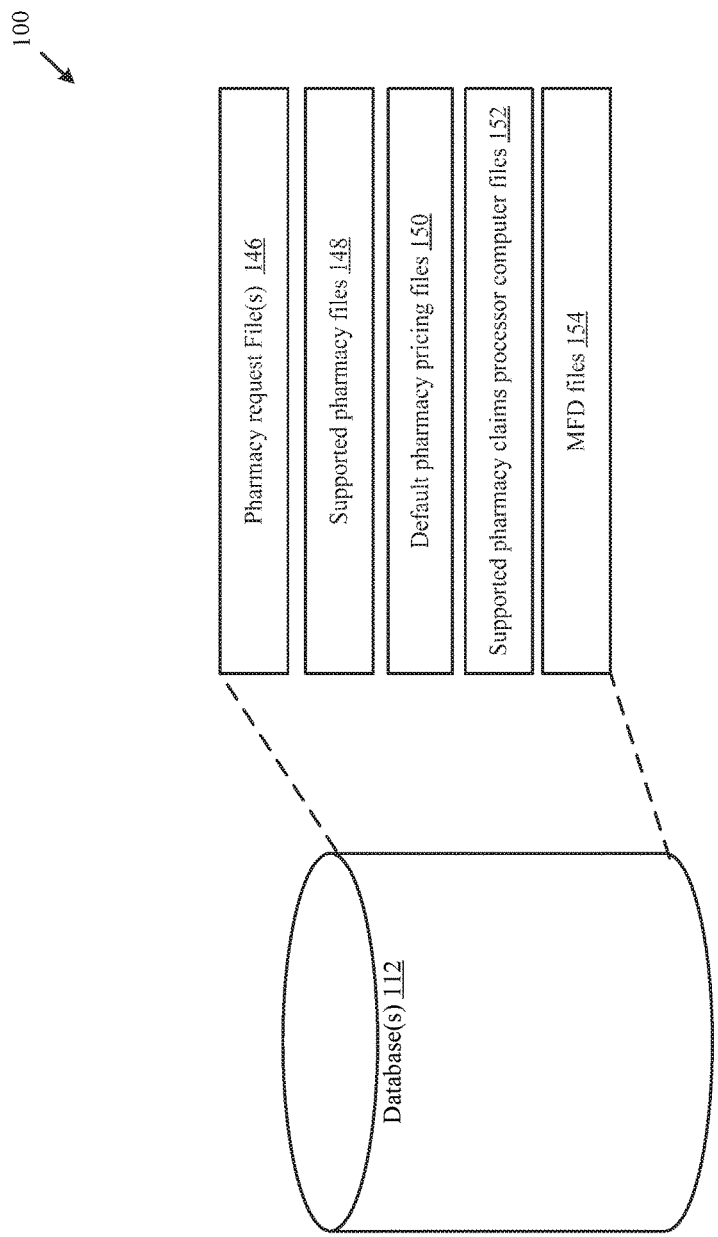

FIG. 1 illustrates an example system 100 for facilitating, among other things, determining and communicating patient pay information or prescription benefit coverage denial information to the prescriber during a process of selecting a medication to be prescribed to the patient, according to one example embodiment of the disclosure. As shown in FIG. 1, the system 100 may include one or more healthcare system devices 102, service provider computers 104, pharmacy claims processor computer 106, EHR vendor/aggregator system 115, and/or pharmacy computers 108. As desired, each of the healthcare provider devices 102, service provider computer 104, pharmacy claims processor computer 106, EHR vendor/aggregator system 115, and/or pharmacy computer 108 may include one or more processing devices that may be configured for accessing and reading associated computer-readable media having stored data thereon and/or computer-executable instructions for implementing various embodiments of the disclosure.

The exemplary healthcare provider device 102 is not intended to be limited to physician's offices alone and may otherwise be associated with any healthcare provider, such as, for example, a prescriber (such as a hospital, urgent care center, clinic, dentist, etc.) or a pharmacist. While the exemplary healthcare provider device 102 references a physician's office, this is for example only and is not intended to be limiting in any manner.

Additionally, in one or more example embodiments of the disclosure, the service provider computers 104 may include or otherwise be in communication with a network benefit check module 110 or benefit check application. The network benefit check module 110 may include computer-executable instructions operable for facilitating the determination of accurate patient pay information or a basis for a prescription benefit coverage denial during a prescription writing process by the prescriber. For example, the network benefit check module 110 may facilitate receipt of a prescription benefit check request. The network benefit check module 110 may facilitate storage of information included in the prescription benefit check request in one or more suitable databases and/or data storage devices 112. For example, the network benefit check module 110 may facilitate the storage of information including, but not limited to, patient information (e.g., a patient identifier (e.g., patient social security number, a subset of the patient social security number, health insurance claim number (HICN), cardholder ID, etc.), name, gender, date of birth), benefits provider identifier (e.g., Banking Identification Number (BIN Number), BIN Number and Processor Control Number (PCN), or BIN Number and Group ID), benefits provider name, date of service, software and/or vendor certification identification, pharmacy identification qualifier, pharmacy identification (e.g., NPI code, DEA number, state license number, NCPDP Provider ID, pharmacy name, pharmacy address, chain name, or the like), product information (e.g., medication, product or service name(s), National Drug Code (NDC) numbers, RxNorm medication identifiers, and the like).

Further, the network benefit check module 110 may facilitate storage of patient information including, but not limited to, medication information (e.g., total number of medications, medication name(s), NDC numbers, RxNorm medication identifiers, quantity of medication to be dispensed, days' supply), patient information (e.g., a patient identifier (e.g., patient social security number, a subset of the patient social security number, health insurance claim number (HICN), cardholder ID, etc.), name, gender, date of birth), and prescriber identification number (e.g., prescriber ID ((e.g., National Provider Identifier (NPI) number and/or Drug Enforcement Agency (DEA) number)), prescriber name, and prescriber ZIP code or other postal zone identifier for a prescription.

In addition to receiving and storing information, the network benefit check module 110 may be further operable to access and/or be in communication with one or more suitable databases and/or data storage devices 112. In one non-limiting example, the benefit check module 110 may also access usual and customary information captured from previously submitted prescription requests, concatenate it with the received one or more prescription requests for use in determining accurate patient pay information or prescription benefit coverage denial information and providing it to the prescriber during a prescription process.

Generally, network devices and systems, including one or more healthcare provider devices 102, service provider computers 104, pharmacy claims processor computers 106, EHR vendor/aggregator system 115, and/or pharmacy computers 108, may include or otherwise be associated with suitable hardware and/or software for transmitting and receiving data and/or computer-executable instructions over one or more communication links or networks. These network devices and systems may also include any number of processors for processing data and executing computer-executable instructions, as well as other internal and peripheral components currently known in the art or which may be developed in the future. Further, these network devices and systems may include or be in communication with any number of suitable memory devices operable to store data and/or computer-executable instructions. By executing computer-executable instructions, each of the network devices may form a special-purpose computer or particular machine. As used herein, the term "computer-readable medium" describes any medium for storing computer-executable instructions.

As shown in FIG. 1, the one or more healthcare provider devices 102, service provider computers 104, pharmacy claims processor computers 106, EHR vendor/aggregator system 115, and/or pharmacy computers 108 may be in communication with each other via one or more networks, such as network 114, which may include one or more independent and/or shared private and/or public networks including the Internet or a publicly switched telephone network. In other example embodiments, one or more components of the system 100 may communicate via direct connections and/or communication links. Each of these components—the healthcare provider device 102, service provider computer 104, pharmacy claims processor computer 106, EHR vendor/aggregator system 115, pharmacy computer 108, and the network 114—will now be discussed in further detail. Although the components are generally discussed as singular components, as may be implemented in various example embodiments, in alternative exemplary embodiments each component may include any number of suitable computers and/or other components.

With continued reference to FIG. 1, one or more healthcare provider devices 102 may be associated with a healthcare provider, for example, a physician, a nurse, a nurse practitioner, a physician's assistant, a hospital, a physician's office, a dentist, etc. A healthcare provider device 102 may be any suitable processor-driven device that facilitates the processing of prescription benefit check requests received from or on behalf of a physician's office (e.g., a prescription benefit check request) for a patient prescription, the communication of prescription benefit check requests or other healthcare requests (either directly or via the EHR vendor/aggregator system 115) to the service provider computer 104, and/or the receipt, processing, and display of responses received (either directly or via the EHR vendor/aggregator system 115) from the service provider computer 104. For example, the healthcare provider device 102 may be a computing device that includes any number of server computers, mainframe computers, networked computers, desktop computers, personal computers, mobile devices, smartphones, digital assistants, personal digital assistants, tablet devices, Internet appliances, application-specific integrated circuits, microcontrollers, minicomputers, and/or any other processor-based devices. The healthcare provider device 102 having computer-executable instructions stored thereon may form a special-purpose computer or other particular machine that is operable to facilitate the processing of transactions/requests for healthcare information made by or on behalf of a healthcare provider and the communication of requested healthcare information, prescription benefit check requests, and other healthcare requests (either directly or via the EHR vendor/aggregator system 115) to the service provider computer 104. Additionally, in certain embodiments, the operations and/or control of the healthcare provider device 102 may be distributed among several processing components. In addition to including one or more processors 116, the healthcare provider device 102 may further include one or more memory devices (or memory) 118, one or more input/output ("I/O") interfaces 120, and one or more network interfaces 122. The memory devices 116 may be any suitable memory devices, for example, caches, read-only memory devices, random access memory devices, magnetic storage devices, removable storage devices, etc. The memory devices 118 may store data, executable instructions, and/or various program modules utilized by the healthcare provider device 102, for example, data files 124, an operating system ("OS") 126, and/or an electronic medical records (EMR) module 128.

The OS 126 may be a suitable software module that controls the general operation of the healthcare provider device 102. The OS 126 may also facilitate the execution of other software modules by the one or more processors 116, for example, the EMR module 128. The OS 126 may be any operating system known in the art or which may be developed in the future including, but not limited to, Microsoft Windows®, Apple OSX™, Apple iOS™ Google Android™, Linux, Unix, or a mainframe operating system.

The EMR module 128 may be a software application(s), including, but not limited to, a dedicated program: for making diagnoses; for determining prescriptions, over-the-counter medications, products or other healthcare services associated with one or more diagnoses; for creating prescription benefit check requests and/or predetermination of benefits requests; for reading and/or updating medical records, as well as interacting with the service provider computer 104. For example, a user 130, such as a healthcare system employee, may utilize the EMR module 128 during a patient visit, for capturing the patient's pharmacy benefit information. Furthermore, the healthcare provider device 102 may utilize the EMR module 128 to retrieve or otherwise receive data, messages, or responses (either directly of via the EHR vendor/aggregator system 115) from the service provider computer 104 and/or other components of the system 100.

At the time of prescribing a product, medication, or service to a patient, the EMR module 128 may engage the provider benefit check module 132 to communicate prescription information in the form of a prescription benefit check request either directly or via the EHR vendor/aggregator system 115) to the service provider computer 104 for use in determining accurate patient pay information or prescription benefit coverage denial information and displaying the retrieved patient pay information or prescription benefit coverage denial information to the prescriber. The provider benefit check module 132 may gather all the required and available optional data including, but not limited to, the medication information (e.g., total number of medications, medication name(s), NDC number(s), RxNorm medication identifiers, etc.), patient information (e.g., patient identifier, patient name, gender, date of birth), and prescriber identification number (e.g., prescriber ID ((e.g., National Provider Identifier (NPI) number or DEA number)), prescriber name, prescriber ZIP code or other postal zone identifier, the patient's preferred pharmacy (e.g., pharmacy name, pharmacy address, pharmacy ID) and the patient's pharmacy benefit information (e.g., BIN Number, Processor Control Number, Group ID, Cardholder ID and/or Person Code). Following the information collection, the provider benefit check module 132 formats one or more prescription benefit check requests for a patient prescription. The one or more prescription benefit check requests may be electronically transmitted (either directly or via the EHR vendor/aggregator system 115) to the service provider computer 104.

The one or more I/O interfaces 120 may facilitate communication between the healthcare provider device 102 and one or more input/output devices, for example, one or more user interface devices, such as a display, keypad, control panel, touch screen display, remote control, microphone, etc., that facilitate user interaction with the healthcare provider device 102. For example, the one or more I/O interfaces 120 may facilitate entry of information associated with a healthcare request by a healthcare provider, such as a physician. The one or more network interfaces 122 may facilitate connection of the healthcare provider device 102 to one or more suitable networks, for example, the network 114 illustrated in FIG. 1. In this regard, the healthcare provider device 102 may receive and/or communicate information to other network components of the system 100, such as the service provider computer 104.

With continued reference to FIG. 1, one or more service provider computers 104 may be associated with a service provider. A service provider computer 104 is a special-purpose switch/router machine that may include, but is not limited to, any suitable processor-driven device that is configured for receiving (either directly or indirectly via the EHR vendor/aggregator system 115), processing, and fulfilling healthcare requests, such as a prescription benefit check request, from the healthcare provider device 102 relating to patient prescription information including, but not limited to, products, medications, or service; medication, product or service name(s), NDC number(s), RxNorm medication identifiers, quantity of medication, product, or service to be dispensed), patient information (e.g., patient identifier, patient name, gender, date of birth), and prescriber identification number (e.g., prescriber ID ((e.g., NPI number or DEA number)), prescriber name, and prescriber ZIP code or other postal zone identifier for a prescription. Any number of healthcare provider devices 102, pharmacy claims processor computers 106, EHR vendor/aggregator systems 115, and/or pharmacy computers 108 may be in communication with the service provider computer 104 as desired in various example embodiments.

The service provider computer 104 may include any number of special-purpose computers or other particular machines, application-specific integrated circuits, microcontrollers, personal computers, minicomputers, mainframe computers, servers, networked computers, and/or other processor-driven devices. The operations of the service provider computer 104 may be controlled by computer-executed or computer-implemented instructions that are executed by one or more processors associated with the service provider computer 104 and form a special-purpose computer or machine that is operable to facilitate the receipt, routing, and/or processing of healthcare requests. The one or more processors that control the operations of the service provider computer 104 may be incorporated into the service provider computer 104 and/or may be in communication with the service provider computer 104 via one or more suitable networks. In certain example embodiments, the operations and/or control of the service provider computer 104 may be distributed among several processing components.

The service provider computer 104 may include one or more processors 134, one or more memory devices 136, one or more input/output ("I/O") interfaces 138, and one or more network interfaces 140. The one or more memory devices 136 may be any suitable memory device, for example, caches, read-only memory devices, etc. The one or more memory devices 136 may store data, executable instructions, and/or various program modules utilized by the service provider computer 104, for example, data files 140 and an operating system ("OS") 144. The OS 144 may be any operating system known in the art or which may be developed in the future including, but not limited to, Microsoft Windows®, Apple OSX™, Linux, Unix, Apple iOS™, Google Android™, or a mainframe operating system. The OS 144 may be a suitable software module that controls the general operation of the service provider computer 104 and/or that facilitates the execution of other software modules.

According to an example embodiment, the data files 142 may store electronic healthcare request records associated with communications received from various healthcare provider devices 102, and/or various pharmacy claims processor computers 106, and/or various pharmacy computers 108. The data files 142 may also store any number of suitable routing tables that facilitate determining the destination of communications received from a healthcare provider device 102 (either directly or indirectly via the EHR vendor/aggregator system 115), a pharmacy claims processor computer 106, and/or a pharmacy computer 108. In one or more example embodiments of the disclosure, the service provider computer 104 may include or otherwise be in communication with one or more suitable databases and/or data storage devices 112 including, but not limited to, one or more pharmacy request files 146 including, one or more default supported pharmacy files 148, one or more default pharmacy pricing files 150, and one or more most frequently (MFD) dispensed files 152.

The one or more pharmacy request files 146 may contain, without limitation, prescription information captured from previously submitted prescription requests. For example, the one or more pharmacy request files 146 may include a product, medication, or service identifier (product, medication, or service; product, medication, or service name(s), NDC number(s), RX Norm, etc.); a quantity of the product, medication, or service to be dispensed; a days' supply, and/or a cost associated with the product, medication, or service.

The one or more pharmacy request files 146 may include one or more supported pharmacy files 148 that may contain, without limitation, one or more pharmacies supported within the healthcare system 100. The one or more supported pharmacy files 148 may include at least a pharmacy identifier (e.g., pharmacy name, chain identifier, NPI code, DEA number, state license number, and/or NCPDP Provider ID), a pharmacy postal code, and/or a pharmacy address. The one or more supported pharmacy files 148 may be utilized by the service provider computer 104, as described here, during the processing of a prescription benefit check request and/or prescription request. The supported pharmacy files 148 may also include a designation of a default pharmacy within a specific postal code. For example, the one or more supported pharmacy files 148 may include a status indicator "DF" for those pharmacies designated as default pharmacies within the associated postal code.

The one or more pharmacy request files 146 may also include one or more default pharmacy pricing files 150 that may contain, without limitation, default price information for specific medications with a specific quantity to be dispensed. The one or more default pharmacy pricing files 150 may be organized by product, medication, and/or service identifier (product, service, or medication ID, product, service, or medication name(s), NDC number(s), RxNorm medication identifiers, etc.) and may include a table correlating a price with a quantity to be dispensed.

Additionally, the one or more pharmacy request files 146 may include one or more MFD files 152 that may contain information supplied by one or more contracted pharmacies, for example, those contracted pharmacies associated with the one or more supported pharmacy files 148. The one or more MFD files 152 may include, without limitation, a table containing most frequently dispensed NDC numbers, most frequently dispensed quantities associated with the most frequently dispensed NDC numbers, and/or a most frequently dispensed days' supply associated with a most frequently dispensed NDC number.

The data storage devices 112 may also include one or more supported pharmacy claims processor computer files 154. The one or more supported pharmacy claims processor computer files 154 may contain, without limitation, information identifying one or more pharmacy claims processor computers 106 supported within the healthcare system 100. The one or more supported pharmacy claims processor computer files 154 may include at least a BIN Number or a BIN Number and Processor Control Number or a BIN Number and Group ID. The one or more supported pharmacy claims processor computer files 154 may also include a list of one or more excluded pharmacy claims processor computers 106. The list of excluded pharmacy claims processor computers may, for example, be organized by BIN Number or BIN Number and Processor Control Number or BIN Number and Group ID.

The service provider computer 104 may include additional program modules for performing other processing methods described herein. Those of ordinary skill in the art will appreciate that the service provider computer 104 may include alternate and/or additional components, hardware, or software without departing from the scope of the disclosure. The management module 156 may be an Internet browser or other software, such as a dedicated program, for interacting with the healthcare provider device 102 (either directly or indirectly via the EHR vendor/aggregator system 115), and/or the pharmacy claims processor computers 106, and/or the pharmacy computer 108. Alternatively, the management module 156 may also be implemented as computer-implemented instructions of a memory of a separate computing entity or processor-based system, according to another example embodiment of the disclosure.

With continued reference to the service provider computer 104, the one or more I/O interfaces 158 may facilitate communication between the service provider computer 104 and one or more input/output devices, for example, one or more user interface devices, such as a display, keypad, control panel, touch screen display, remote control, microphone, etc., that facilitate user interaction with the service provider computer 104. The one or more network interfaces 160 may facilitate connection of the service provider computer 104 to one or more suitable networks, for example, the network 114 illustrated in FIG. 1. In this regard, the service provider computer 104 may communicate with other components of the system 100.

With continued reference to FIG. 1, any number of pharmacy claims processor computers 106 may be associated with any number of pharmacy benefit managers and/or processors. Each pharmacy claims processor computer may be any suitable processor-driven devices, such as, but not limited to, a server computer, a personal computer, a laptop computer, a handheld computer, and the like. In addition to having one or more processors 162, the pharmacy claims processor computer 106 may further include one or more memories 164, one or more input/output (I/O) interfaces 166, and one or more network interfaces 168. The memory 164 may store data files 170 and various program modules, such as an operating system (OS) 172 and a benefits management module 174. The I/O interface(s) 166 may facilitate communication between the processors 162 and various I/O devices, such as a keyboard, mouse, printer, microphone, speaker, monitor, bar code reader/scanner, RFID reader, and the like. The network interface(s) 170 each may take any of a number of forms, such as a network interface card, a modem, a wireless network card, and the like.

Generally, the pharmacy claims processor computer 106 may facilitate the determination of benefits, coverage, and/or extent of coverage for one or more prescription requests, such as prescription claim requests, pharmacy billing requests, predetermination of benefits requests or other billing requests. According to various embodiments, the pharmacy claims processor computer 106 may be associated with, without limitation, a PBM, an insurance company, a government payor affiliated entity, another third-party payor, or a pharmacy claims processor processing prescription requests and performing processing on the prescription requests on behalf of one or more third-party payors and/or healthcare providers.

The pharmacy claims processor computer 106 may include the benefits management module 174. The benefits management module 174 may be an Internet browser or other software, such as a dedicated program, for interacting with the service provider computer 104 and/or the pharmacy computer 108. The benefits management module 174 may be operable to access one or more databases in database 112. In one non-limiting example, the pharmacy claims processor computer 106 may have a dedicated connection to the database 112 or another similarly configured database. However, the pharmacy claims processor computer 106 may also communicate with the database 112 via the network 114 shown, or via another network.

With continued reference to FIG. 1, any number of pharmacy computers 108 may be associated with any number of pharmacies and/or pharmacists. Each pharmacy computer 108 may be any suitable processor-driven device that facilitates receiving, processing, and/or fulfilling prescription requests and/or prescription responses received from the service provider computer 104. For example, a pharmacy computer 108 may be a processor-driven device associated with (e.g., located within) a pharmacy. As desired, the pharmacy computer 108 may include any number of special-purpose computers or other particular machines, application-specific integrated circuits, microcontrollers, personal computers, minicomputers, mainframe computers, servers, and the like. In certain example embodiments, the operations of the pharmacy computer 108 may be controlled by computer-executed or computer-implemented instructions that are executed by one or more processors associated with the pharmacy computer 108 to form a special-purpose computer or other particular machine that is operable to facilitate the receipt, processing, and/or fulfillment of prescription requests (e.g., a prescription claim request, a billing request, pharmacy billing request, or predetermination of benefits request) received from the service provider computer 104. The one or more processors that control the operations of a pharmacy computer 108 may be incorporated into the pharmacy computer 108 and/or may be in communication with the pharmacy computer 108 via one or more suitable networks. In certain example embodiments, the operations and/or control of the pharmacy computer 108 may be distributed among several processing components.

Similar to other components of the system 100, each pharmacy computer 108 may include one or more processors 176, one or more memory devices 178, one or more I/O interfaces 180, and one or more network interfaces 182. The one or more memory devices 178 may be any suitable memory devices, for example, caches, read-only memory device, random access memory devices, magnetic storage devices, removable memory devices, etc. The one or more memory devices 178 may store data, executable instructions, and/or various program modules utilized by the pharmacy computer 108, for example, data files 184, an OS 186, and a pharmacy management module 188. The data files 184 may include any suitable information that is utilized by the pharmacy computer 108. The OS 186 may be a suitable software module that controls the general operation of the pharmacy computer 108. The OS 186 may also facilitate the execution of other software modules by the one or more processors 176. The OS 186 may be any operating system known in the art or which may be developed in the future including, but not limited to, Microsoft Windows®, Apple OSX™ Linux, Unix, Apple iOS™, Google Android™, or a mainframe operating system.

The one or more I/O interfaces 180 may facilitate communication between the pharmacy computer 108 and one or more input/output devices, for example, one or more user interface devices, such as a display, keypad, control panel, touch screen display, remote control, microphone, etc., that facilitate user interaction with the pharmacy computer 108. The one or more network interfaces 182 may facilitate connection of the pharmacy computer 108 to one or more suitable networks, for example, the network 114 illustrated in FIG. 1. In this regard, the pharmacy 108 may receive prescription responses and/or other communications from the service provider computer 104 and the pharmacy computer 108 may communicate information associated with processing prescription requests to the service provider computer 104.

The pharmacy management module 188 may be a software application(s), including a dedicated program, for fulfilling healthcare transaction orders, reading and/or updating medical records (e.g., prescription records), facilitating patient billing, etc., as well as interacting with the service provider computer 104. For example, a pharmacist or other pharmacy employee, may utilize the pharmacy management module 188 in filling a prescription, recording and/or updating a patient's medical prescription history, billing a patient, and preparing and providing a prescription request for information to the service provider computer 104. Furthermore, the pharmacy computer 108 may utilize the pharmacy management module 188 to retrieve or otherwise receive data, messages, or responses from the healthcare provider device 102 and/or other components of the system 100.

With continued reference to FIG. 1, the system 100 may include any number of EHR vendor/aggregator systems 115. Each EHR vendor/aggregator system 115 may be associated with any number of healthcare provider devices and computer systems 102. For example, each EHR vendor/aggregator system 115 can be a vendor of EHR programs and systems provided to multiple healthcare providers and/or an aggregator of EHR data from the multiple healthcare providers and can act as a conduit for electronic requests and/or responses electronically communicated between the healthcare provider device 102 and the service provider computer 104 via the network 114. In certain example embodiments, the EHR vendor/aggregator 115 provides a single-point access for the electronic transmission of data and electronic requests associated with or using a healthcare provider's electronic medical records system to the service provider computer 104 via the prescriber/healthcare provider device 102.

The network 114 may include any telecommunication and/or data network, whether public, private, or a combination thereof, including a local area network, a wide area network, an intranet, the Internet, intermediate handheld data transfer devices, and/or any combination thereof and may be wired and/or wireless, or any combination thereof. The network 114 may also allow for real time, offline, and/or batch requests to be transmitted between or among the healthcare provider device 102, the service provider computer 104, the pharmacy claims processor computer 106, EHR vendor/aggregator system 115, and the pharmacy computer 108. Various methodologies as described herein, may be practiced in the context of distributed computing environments. Although the service provider computer 104 is shown for simplicity as being in communication with the healthcare provider device 102 (either directly or indirectly via the EHR vendor/aggregator system 115), the pharmacy claims processor computer 106, or the pharmacy computer 108 via one intervening network 114, it is to be understood that any other network configurations are possible. For example, intervening network 114 may include a plurality of networks, each with devices such as gateways and routers for providing connectivity between or among the components of the system 100. Instead of or in addition to the network 114, dedicated communication links may be used to connect various devices in accordance with an example embodiment. For example, the service provider computer 104 may form the basis of network 114 that interconnects the healthcare provider device 102, the service provider computer 104, the pharmacy claims processor computer 106, EHR vendor/aggregator system 115, and the pharmacy computer 108.

Those of ordinary skill in the art will appreciate that the system 100 shown in and described with respect to FIG. 1 is provided by way of example only. Numerous other operating environments, system architectures, and device and network configurations are possible. Other system embodiments can include fewer or greater numbers of components and may incorporate some or all of the functionality described with respect to the system components shown in FIG. 1. For example, in an exemplary embodiment, the service provider computer 104 (or other computer) may be implemented as a specialized processing machine that includes hardware and/or software for performing the methods described herein. Accordingly, embodiments of the disclosure should not be construed as being limited to any particular operating environment, system architecture, or device or network configuration.

Operational Overview

Certain portions of the example methods below will be described with reference to determining and communicating a prescription benefit check response message generated during the processing of a prescription request. In one example implementation, the prescription request may include a healthcare claim transaction, a predetermination of benefits request; a prescription claim request, a billing request, or a pharmacy billing request. While the methods described below are described with reference to a prescription request or certain types of prescription requests, each form of prescription request should be individually read as being used in the methods described below.

Figure 2:
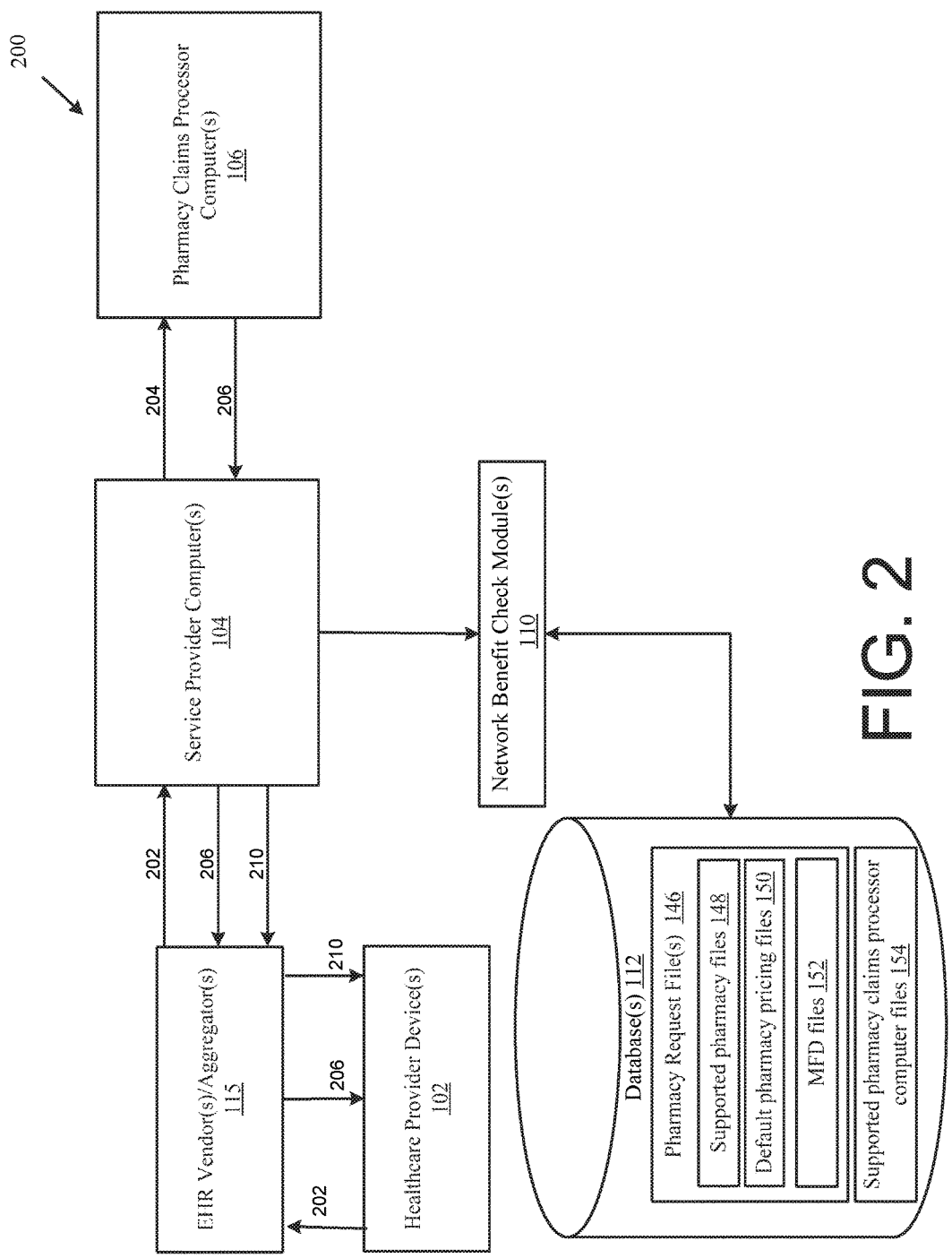
FIG. 2 is a block diagram for receiving and communicating a prescription benefit check request, according to one exemplary embodiment.
Figure 3A:
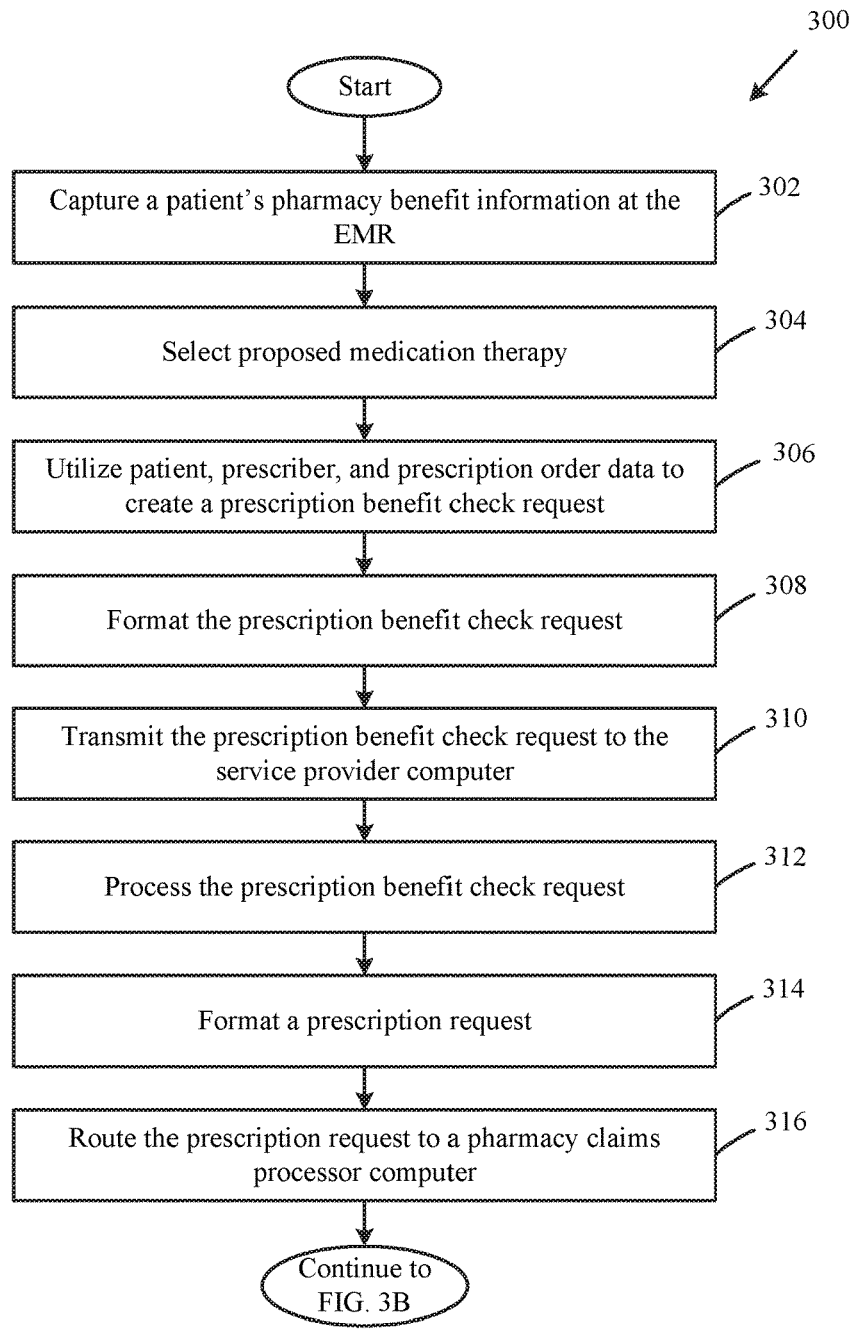
FIGS. 3A and 3B illustrate a flow chart of an example method for receiving and communicating a prescription benefit check request, according to one exemplary embodiment.
Figure 3B:
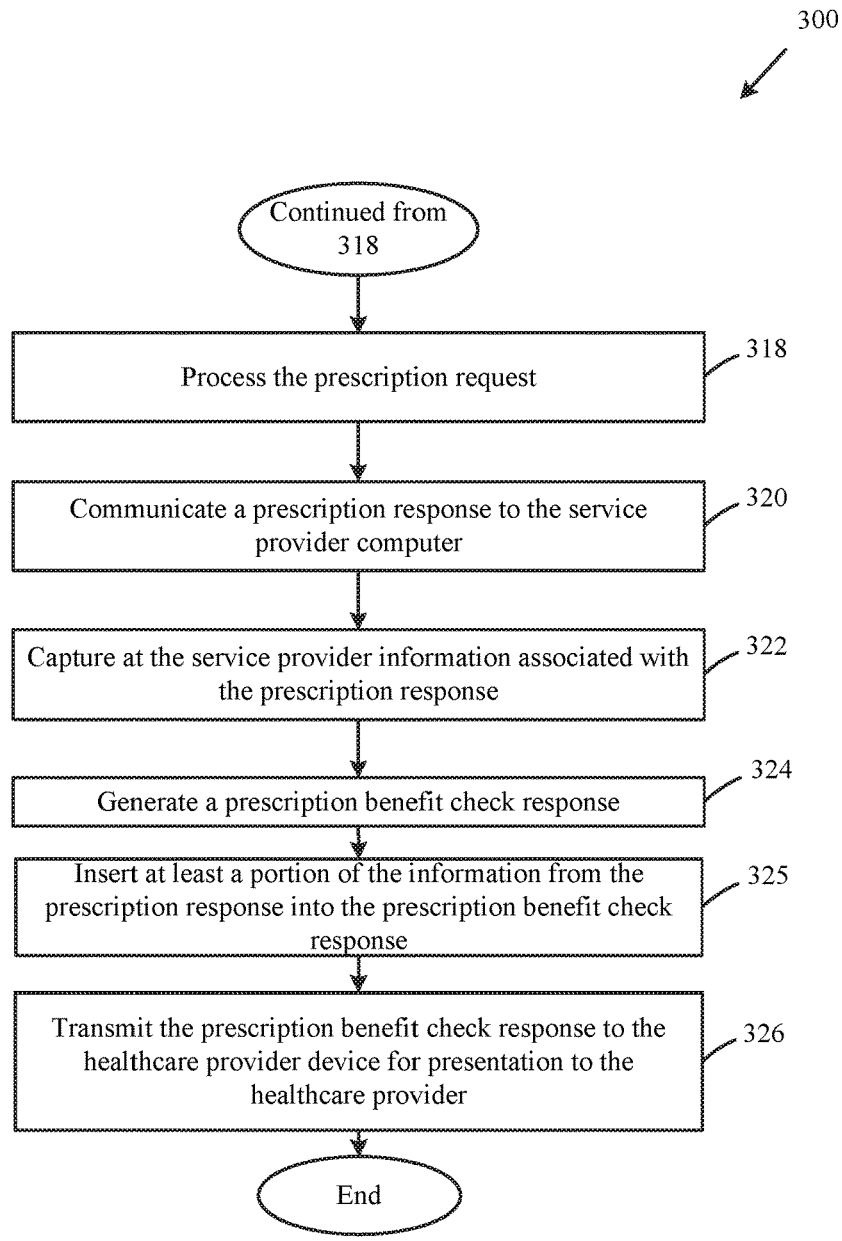

FIG. 2 illustrates an example block diagram 200 for receiving and communicating a prescription benefit check request according to an example embodiment of the disclosure. FIGS. 3A and 3B illustrate an example method 300 for receiving and communicating a prescription benefit check request, according to an example embodiment of the disclosure. The block diagram 200 of FIG. 2 will be discussed in conjunction with the method of 300 of FIGS. 3A and 3B.

Referring now to FIGS. 1A, 1B, 2, 3A, and 3B the exemplary method 300 begins at the START step and continues to step 302, where the healthcare provider device, such as the healthcare provider device 102, may be utilized to capture a patient's pharmacy benefit information. In one example implementation, the healthcare provider device 102 may employ an electronic medical records (EMR) module 128 to capture the patient's pharmacy benefit information. The patient's pharmacy benefit information may be captured as a part of a patient visit. For example, the patient's pharmacy benefit information may be captured as a part of an administrative function at the point of a patient admission (e.g., a patient registration). Alternatively, the patient's pharmacy benefit information may be captured at a time other than the patient visit. For example, the patient may communicate pharmacy benefit information utilizing a web-based portal from any patient-desired location. Generally, the patient pharmacy benefit information may be found on a patient's pharmacy benefit card (e.g., insurance card). In one non-limiting example, the EMR module 128 may capture from a patient's pharmacy benefit card, without limitation, a BIN Number, a Processor Control Number, an assigned Cardholder ID, Person Code, Relationship Code, and/or a Group ID. Additional patient information not generally included on the patient's pharmacy benefit card that may be captured by the EMR includes, without limitation, a patient's date of birth and/or a patient gender code.

At step 304, a prescriber may select a proposed product, service, or medication therapy. Hereinafter, the methods will be described with reference to a medication therapy and a medication prescription. However, this is for example purposes only as other product or service therapies and corresponding product or service prescriptions may be substituted therefore and should be individually read as being used in the methods herein. In one non-limiting example, the proposed medication therapy may include a medication identifier (e.g., a National Drug Code (NDC) identification, RxNorm medication identifiers, a medication name, and the like).

At step 306 the healthcare provider device 102 creates a prescription benefit check request 202. In one non-limiting example, the prescription benefit check request 202 may be a proprietary transaction and the healthcare provider device 102 may employ a provider benefit check module 132 to create the prescription benefit check request 202. The prescription benefit check request 202 may include, without limitation, the patient pharmacy benefit information, proposed medication therapy, patient information, as well as prescriber information.

In one non-limiting example, the provider benefit check module 132 may automatically gather the patient information, the patient pharmacy benefit information, the proposed medication therapy, and the prescriber information. The patient information, patient pharmacy benefit information, proposed medication therapy, and the prescriber information gathered by the provider benefit check module 132 may include, without limitation, the medication identifier, a total number of medications selected by the prescriber, the BIN Number, the Processor Control Number, a pharmacy ID (e.g., NPI code, DEA number, state license number, NCPDP Provider ID, etc. for a patient's pharmacy of choice, the pharmacy closest to the prescriber's location or a default pharmacy within a predetermined distance of the prescriber location), the Cardholder ID, the Group ID, the Person Code, the patient's date of birth, the patient's gender code, the patient's first name, the patient's last name, a medication identifier (e.g., a National Drug Code (NDC) identification, RxNorm medication identifiers, a medication name, and the like), a prescriber ID, a prescriber's last name, and/or a prescriber's postal code.

At step 308, the healthcare provider device 102 may format the prescription benefit check request 202. In one non-limiting example, the healthcare provider device 102 may employ the provider benefit check module 132 to format the prescription benefit check request 202. In one non-limiting example, the provider benefit check module 132 may format the field and source of data included in the prescription benefit check request 202. For example:

Field: Source

Medication #: EMR module 126

Total Medications: EMR module 126

Medication Quantity: EMR module 126

Medication Days' Supply: EMR module

BIN Number: EMR module 126/patient pharmacy benefit card/patient profile

Processor Control Number: EMR module 126/patient pharmacy benefit card/patient profile Pharmacy ID: EMR module 126/patient profile Cardholder ID: EMR module 126/Patient pharmacy benefit card/patient profile Group ID: EMR module 126/Patient pharmacy benefit card/patient profile Person Code: EMR module 126/Patient pharmacy benefit card/patient profile Date of Birth: EMR module 126/patient profile Patient Gender Code: EMR module 126/patient profile Patient First Name: EMR module 126/Patient pharmacy benefit card/patient profile Patient Last Name: EMR module 126/Patient pharmacy benefit card/patient profile Product Service ID EMR module 126/patient profile Prescriber ID: EMR module 126/prescriber profile Prescriber Last Name: EMR module 126/prescriber profile Prescriber Postal Code: EMR module 126/prescriber profile At step 310, the healthcare provider device 102 may communicate the prescription benefit check request 202 (either directly or indirectly via the EHR vendor/aggregator system 115) to the service provider computer 104. In one example implementation, the healthcare provider device 102 may employ the provider benefit check module 132 to transmit the prescription benefit check request 202 to the EHR vendor/aggregator system 115 which forwards the prescription benefit check request 202 to the service provider computer 104 via one or more suitable networks 114 (e.g., a wide area network, the Internet, a cellular network, etc.).

At step 312, the service provider computer 104 may process the prescription benefit check request 202. In one non-limiting example, the service provider computer 104 may employ a network benefit check module 110 to process the prescription benefit check request 202. In one example, the processing of the prescription benefit check request 202 may include, without limitation, a determination of (i) whether the included Pharmacy ID associated with the patient's preferred pharmacy is a contracted pharmacy; (ii) whether all of the required patient and/or prescriber information is included in the prescription benefit check request 202; and/or (iii) whether the BIN Number or BIN Number and Processor Control Number or BIN Number and Group ID included in the prescription benefit check request 202 is a supported BIN Number or BIN Number and Processor Control Number or BIN Number and Group ID.

Processing of the prescription benefit check request 202 may further include a determination of a corresponding pharmacy claims processor computer 106 and whether the determined pharmacy claims processor computer 106 is supported by the system described in FIG. 1. Processing of the prescription benefit check request 202 may also include identifying the request type of the prescription benefit check request 202. For example, based upon the determination of the destination pharmacy claims processor computer 106, the system may determine the type and format of a prescription request to be generated by the service provider computer 104 in order to identify information for a response to the prescription benefit check request 202. Examples of the prescription request can include, but are not limited to a pharmacy billing request (e.g., request type "B1"); (ii) a billing request (e.g., request type "P1"); (iii) a predetermination of benefits request (e.g., request type "D1"); and/or (iv) a request type not supported by the system described in FIG. 1.

Processing of the prescription benefit check request 202 may further include accessing one or more pharmacy request files 146. The one or more pharmacy request files 146 may include, without limitation, prescription information captured from previously submitted prescription requests. For example, the one or more pharmacy request files 146 may include a medication identifier (medications, medication name(s), NDC number(s), RxNorm medication identifiers, and the like), and/or a quantity of medication to be dispensed, a cost associated with the medication and/or the quantity of medication to be dispensed.

At step 314, the service provider computer 104 may, in response to receiving and evaluating the prescription benefit check request 202, format a corresponding prescription request 204. In one non-limiting example, the service provider computer 104 may employ a network benefit check module 110 to reformat the prescription benefit check request 202 into a prescription request 204. Alternatively, a new prescription request 204 may be generated and all or a portion of the information in the prescription benefit check request 202 may be inserted into the prescription request 204 by the network benefit check module 110. At step 316, the service provider computer 104 may route the prescription request 204 to the determined pharmacy claims processor computer 106.

At step 318, the pharmacy claims processor computer 106 may process the prescription request. In one example implementation, the adjudication may include a determination of whether the prescription request 204 was approved or denied. At step 320, the pharmacy claims processor computer 106 may communicate a prescription response 206 to the service provider computer 104. The prescription response 206 may also include, without limitation, a response type (e.g., a pharmacy billing request, a billing request, a predetermination of benefits request, etc.) and/or a response status associated with whether the prescription request 204 was approved or denied. In one example implementation, when the prescription request 204 is approved, the prescription response 206 may have a response status of "P" (or a number of other response status indicators known to those of ordinary skill in the art). If, however, the prescription request 204 is denied, the prescription response 206 may have a response status of "R" (or a number of other response status indicators known to those of ordinary skill in the art).

In one non-limiting example, when the prescription response 206 includes a response status of "P" (or a number of other response status indicators indicator an approved or paid response), the prescription response 206 may also include, without limitation, one or more fields comprising a patient pay amount field populated with a value ("patient pay") returned by the pharmacy claims processor computer 106, an associated dispense quantity field populated with a submitted quantity dispensed on the prescription request 204, a usual and customary charge field populated with the submitted usual and customary charge on the prescription request 204, a pharmacy name field populated with a short pharmacy name corresponding to the submitted pharmacy ID on the prescription request 204, and/or a pharmacy street address populated with a pharmacy street address corresponding to the submitted pharmacy ID on the prescription request 204.

If, on the other hand, the prescription response 206 includes the response status of "R" (or a number of other response status indicators known to those of ordinary skill in the art) indicating the prescription request was denied, the prescription response 206 may also include, without limitation, one or more fields comprising the patient pay amount field left blank, the associated dispense quantity field is left blank, a reason for denial code field populated with a denial error code identifying the reason the prescription request 204 was denied (e.g., code "70" that represents a product/service not covered—plan/benefit exclusion, code "75" that represents prior authorization required, code "76" that represents plan limitations exceeded, code "MR" that represents a product not on formulary, code "60" that represents a product/service not covered for patient age, code "73" that represents a denial due to refills not covered, code "608" that represents a denial for step therapy—alternate drug therapy required prior to use of the submitted product, code "AC" that represents a product not covered—non-participating manufacturer, code "61" that represents a product/service not covered for the patient gender in the request, code "88" that represents a drug utilization review (DUR) denial error, code "78" that represents a denial because the cost exceeds maximum, code "79" that represents a denial for a refill too soon, code "7X" that represents a denial because the days' supply exceeds plan limitation, code "ZZ" that represents a denial because the cardholder ID submitted is inactive—new cardholder ID on file, code "77" that represents a denial due to a discontinued product/service ID number, code "65" that represents a denial because the patient is not covered, code "52" that represents a denial for a non-matched cardholder ID); a denial reason field populated with a denial reason corresponding to the denial error code for the denied prescription request 204 (e.g., product/service not covered—plan/benefit exclusion, prior authorization required, plan limitations exceeded, product not on formulary, product/service not covered for patient age, refills not covered, step therapy—alternate drug therapy required prior to use of the submitted product, product not covered—non-participating manufacturer, product/service not covered for patient gender, DUR reject error, cost exceeds maximum, refill too soon, days' supply exceeds plan limitation, cardholder ID submitted is inactive—new cardholder ID on file, discontinued product/service ID number, patient is not covered, non-matched cardholder ID, pricing not available for an identified scenario, or the like), the usual and customary charge field is left blank, the pharmacy name field is left blank, and/or a reason for denial description field populated with an abbreviated description of the corresponding reason for denial code. The denial codes and associated descriptions are provided above for example purposes only. Other denial codes and associated descriptions may also be included while some of the denial codes and associated responses provided may be removed as desired in a particular system.

At step 322, the service provider computer 104 may capture information associated with the one or more fields included in the prescription response 206. In one non-limiting example, the service provider computer 104 may employ a network benefit check module 110 to capture information associated with the one or more fields included in the prescription response 206. For example, for an approved response (e.g., the response status is identified as "P" (or a number of other response status indicators known to those of ordinary skill in the art)), the service provider computer 104 may (i) identify the response type (e.g., a pharmacy billing request, predetermination of benefits request, or a billing request); (ii) determine the status of the prescription response (iii) determine if there is a pharmaceutical manufacturer message to deliver; (iv) capture the response for the corresponding prescription request 204 to submit a subsequent reversal request; and/or (v) format an approved prescription benefit check response. In another example, for a denial response (e.g., the response status is identified as "R" (or a number of other response status indicators known to those of ordinary skill in the art)), the service provider computer may (i) identify the response type (e.g., a pharmacy billing response, predetermination of benefits response, or a billing response); (ii) determine the status of the prescription response (iii) determine if there is a pharmaceutical manufacturer message to deliver; (iv) determine the denial error code; (v) determine if a reason for denial message is included that provides an explanation for why the prescription request 204 was denied and/or (v) format a denied prescription benefit check response including the denial error code and any other information from the prescription request 204 describing why the prescription request 204 was denied (e.g., information in the reason for denial message).

For example, the prescription response 206 may include:
Request type "B1" (e.g., a pharmacy billing request type), "D1" (e.g., predetermination of benefits request type, or "P1" (e.g., a prescriber billing request type)
Response status "P" (e.g., approved or paid) (or a number of other response status indicators known to those of ordinary skill in the art)
Patient pay amount
Associated dispense quantity
Associated dosage form
Pharmacy claims processor computer message
Pharmaceutical manufacturer message
Enhanced eVoucherRx Applied (if applied)
Pharmacy name In one non-limiting example, the pharmacy claims processor computer message and/or the pharmaceutical manufacturer message may be limited to a predetermined field length (e.g., 40 characters). If the pharmacy claims processor computer message and/or the pharmaceutical manufacture message exceed the predetermined field length, a "more information" indicator may be displayed indicating that there is an additional portion to the pharmacy claims processor computer message and/or the pharmaceutical manufacturer message. The pharmacy claims processor computer message and/or the pharmaceutical manufacturer message may have a predetermined maximum field length (e.g., 200 characters).

At step 324, the service provider computer (e.g., the network benefit check module 110) can generate a prescription benefit check response 210. The network benefit check module 110 can insert all or a portion of the information from the prescription response 206 into the prescription benefit check response 210 at step 325. The prescription benefit check response 210 may then be transmitted from the service provider computer 104 to the healthcare provider device 102, either directly or indirectly via the EHR vendor/aggregator 115, at step 326. The healthcare provider device 102 may then display the prescription benefit check response 210. If the prescription benefit check response 210 is based on an approved ("P" (or a number of other response status indicators known to those of ordinary skill in the art)) prescription response 206 corresponding to a request type (e.g., "B1"), the prescription benefit check response 210 may be displayed as:
Response type—B1
Response status—P (or a number of other response status indicators known to those of ordinary skill in the art)
Patient Pay Amount—Yes
Associated dispense quantity—Yes
Associated dosage form—Yes
Service provider computer message—No
Pharmacy claims processor computer message—No
Pharmaceutical manufacturer message—Optional
Denial Reason—No
Enhanced eVoucherRx Applied—Y or N
Pharmacy Name—Yes
Reason for denial message—No If the prescription benefit check response 210 is based on an approved ("P" (or a number of other response status indicators known to those of ordinary skill in the art))

prescription response 206 corresponding to a billing request type (e.g., "P1"), the prescription benefit check response 210 may be displayed as:
  Response type—P1
  Response status—P (or a number of other response status indicators known to those of ordinary skill in the art)
  Patient pay amount—Yes
  Associated dispense quantity—Yes
  Associated dosage form—Yes
  Service provider computer message—No
  Pharmacy claims processor computer message—Optional
  Pharmaceutical manufacturer message—Optional
  Denial reason—No
  Enhanced eVoucherRx applied—Y or N
  Pharmacy Name—Yes
  Reason for denial—No If the prescription benefit check response 210 is based on an approved ("B" (or a number of other response status indicators known to those of ordinary skill in the art)) prescription response 206 corresponding to a predetermination of benefits request type (e.g., "D1"), the prescription benefit check response 210 may be displayed as:
  Response type—D1
  Response status—B (or a number of other response status indicators known to those of ordinary skill in the art)
  Patient pay amount—TBD
  Associated dispense quantity—TBD
  Associated dosage form—TBD
  Service provider computer message—No
  Pharmacy claims processor computer message—TBD
  Pharmaceutical manufacturer message—TBD
  Denial reason—TBD
  Enhanced eVoucherRx applied—TBD
  Pharmacy Name—TBD
  Reason for denial—TBD If the prescription benefit check response 210 is based on a denied ("R" (or a number of other response status indicators known to those of ordinary skill in the art)) prescription response 206 corresponding to a pharmacy billing request (e.g., "B1"), the prescription benefit check response 210 may be displayed as:
  Response type—B1
  Response status—R (or a number of other response status indicators known to those of ordinary skill in the art)
  Patient Pay Amount—No
  Associated dispense quantity—No
  Associated dosage form—No
  Service provider computer message—Optional
  Pharmacy claims processor computer message—No
  Pharmaceutical manufacturer message—Optional
  Denial Reason—Yes (e.g., a denial error code)
  Pharmacy Name—No
  Reason for denial message—Optional (e.g., a description of the reason for denial associated with the denial error code)

If the prescription benefit check response 210 is based on a denied ("R" (or a number of other response status indicators known to those of ordinary skill in the art)) prescription response 206 corresponding to a billing request type (e.g., "P1"), the prescription benefit check response 210 may be displayed as:
  Response type—P1
  Response status—R (or a number of other response status indicators known to those of ordinary skill in the art)
  Patient pay amount—No
  Associated dispense quantity—No
  Associated dosage form—No
  Service provider computer message—Optional
  Pharmacy claims processor computer message—Optional
  Pharmaceutical manufacturer message—Optional
  Denial reason—Yes (e.g., a denial error code)
  Enhanced eVoucherRx applied—No
  Pharmacy Name—No
  Reason for denial—Optional (e.g., a description of the reason for denial associated with the denial error code)

If the prescription benefit check response 210 is based on a denied ("R" (or a number of other response status indicators known to those of ordinary skill in the art)) prescription response 206 corresponding to a predetermination of benefits request type (e.g., "D1"), the prescription benefit check response 210 may be displayed as:
  Response type—D1
  Response status—R (or a number of other response status indicators known to those of ordinary skill in the art)
  Patient pay amount—TBD
  Associated dispense quantity—TBD
  Associated dosage form—TBD
  Service provider computer message—No
  Pharmacy claims processor computer message—TBD
  Pharmaceutical manufacturer message—TBD
  Denial reason—TBD
  Enhanced eVoucherRx applied—TBD
  Pharmacy Name—TBD
  Reason for denial—TBD The method 300 may end after step 326.

Figure 4A:
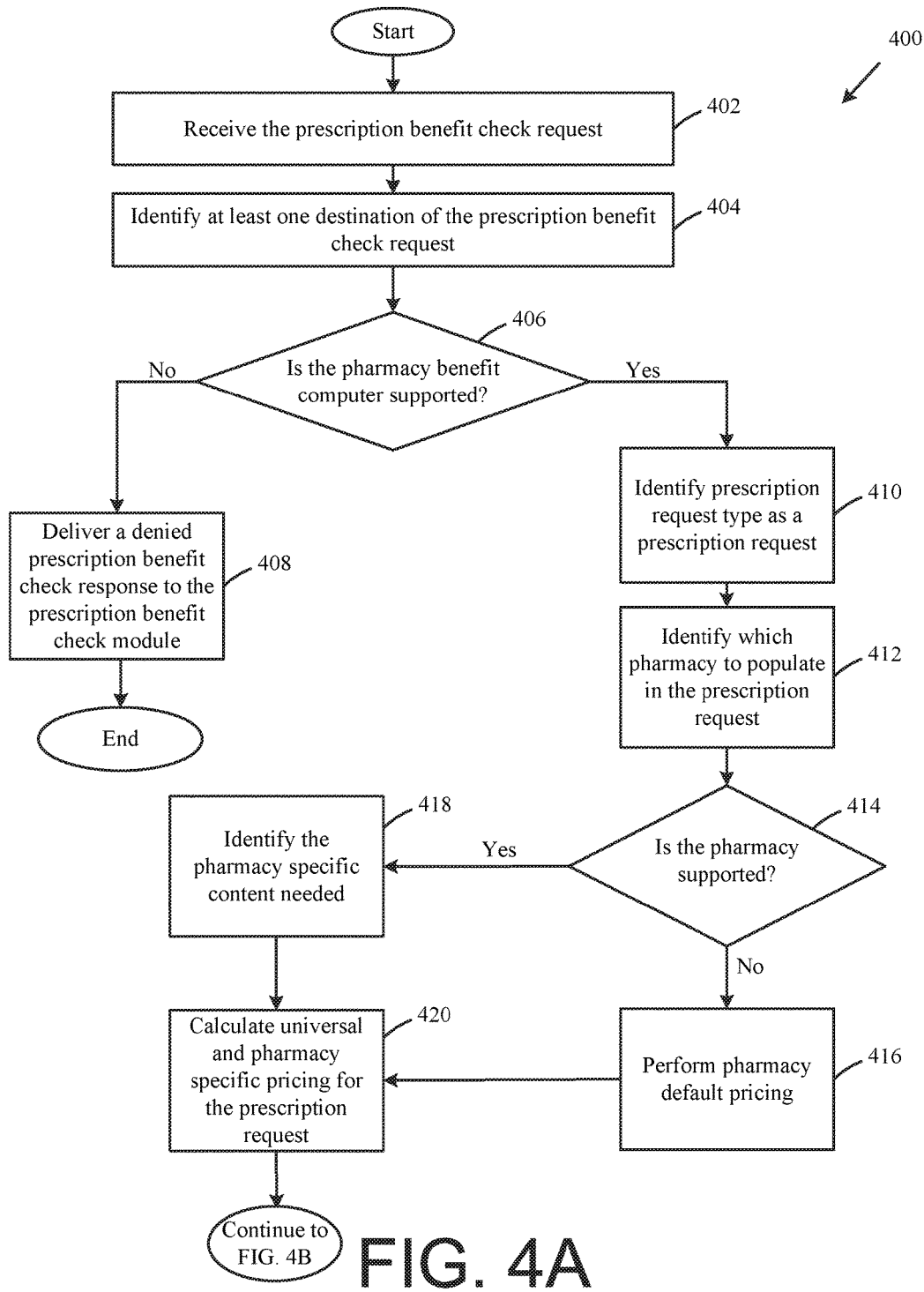
FIGS. 4A and 4B illustrate a flow chart of an example method for determining the request type of the prescription benefit check request as a pharmacy billing request and processing the determined pharmacy billing request, according to one exemplary embodiment.
Figure 4B:
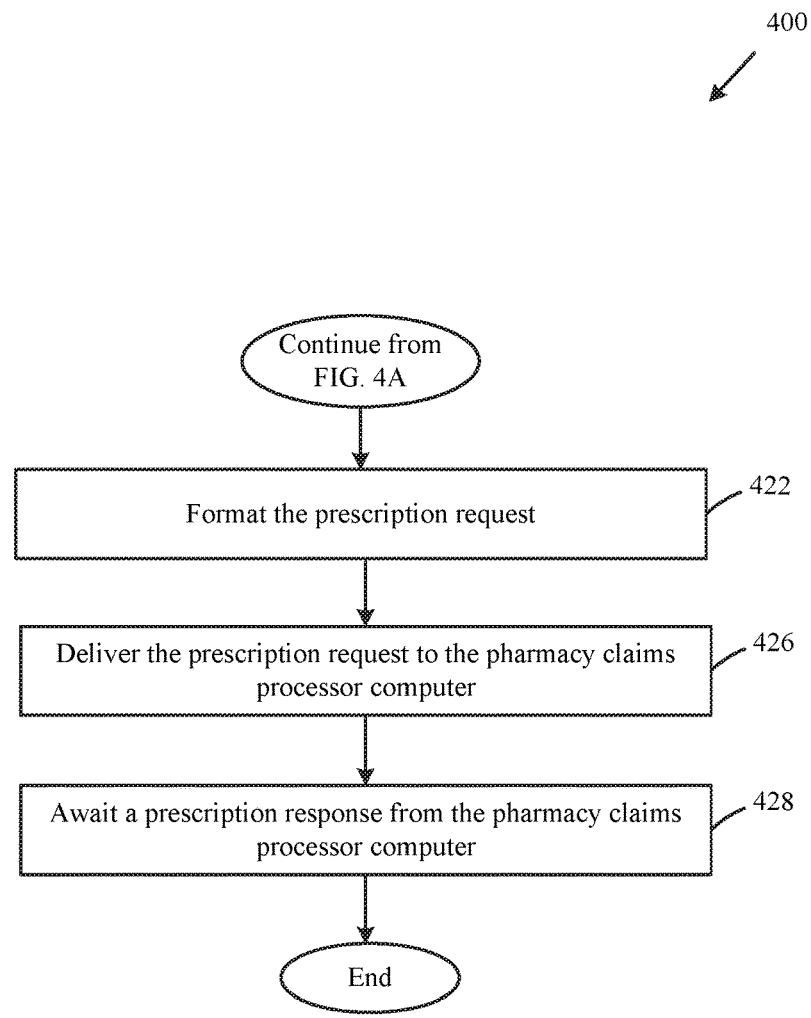

FIG. 4 illustrates an example method 400 for determining the request type of the prescription benefit check request 202 as a prescription request generally formatted as a pharmacy billing request using the NCPDP Telecom standard and processing the prescription request. The block diagram 200 of FIG. 2 will be discussed in conjunction with the method 400.

Referring now to FIGS. 1A, 1B, 2, 3A, 3B, 4A, and 4B the exemplary method 400 begins at the START step and continues to step 402, where the service provider computer 104 may receive the prescription benefit check request 202. At step 404, the service provider computer 104 may identify at least one destination of the prescription benefit check request 202. In one non-limiting example, the destination of the prescription benefit check request may be the pharmacy claims processor computer 106. The pharmacy claims processor computer 106 may be identified using the BIN Number or the BIN Number and Processor Control Number or the BIN Number and Group ID included in the prescription benefit check request 202.

At step 406, the service provider computer 104 may determine whether the identified pharmacy claims processor computer 106 is a supported pharmacy claims processor computer 106 within the system 100. In one non-limiting example, the service provider computer 104 may access one or more supported pharmacy claims processor computer files 154 to determine whether the identified pharmacy claims processor computer 106 is a supported destination. For example, the service provider computer 104 may employ the network benefit check module 110 to access one or more supported pharmacy claims processor computer files 154. The network benefit check module 110 may compare the submitted BIN Number or the BIN Number and Processor Control Number or the BIN Number and Group ID on one or more tables within one or more supported pharmacy claims processor computer files 154 to determine if a match exists. The one or more tables may include, without limitation, a BIN Number field, a Processor Control Number field, a Group ID field and/or a support designation field including a support indicator (e.g., a "Y" for supported or a "N" for not supported). The network check module 110 may parse the one or more supported pharmacy claims processor computer files 154 to identify whether the BIN Number or BIN Number and Processor Control Number or BIN Number and Group ID exists in the one or more tables. If the BIN Number or the BIN Number and Processor Control Number or the BIN Number and Group ID exists in the one or more supported pharmacy claims processor computer files 154 (a match), and a "Y" support indicator accompanies the existing file, then the YES branch is followed and processing may proceed to step 410. If the BIN Number or the BIN Number and Processor Control Number or the BIN Number and Group ID does not exist in the one or more supported pharmacy claims processor computer files 154 (no match), and/or a "N" support indicator accompanies the existing file, then the NO branch is followed and processing may proceed to step 408.

At step 408, the service provider computer 104 may deliver a denied prescription benefit check response 208 to the healthcare provider device 102. The denied prescription benefit check response 208 can include a denial error code in a denial reason field of the denied prescription benefit check response 208 and optionally a further textual explanation of why the prescription benefit check request 202 was denied. The method 400 may end after step 408.

At step 410, the service provider computer 104 may determine the type and format of a prescription request to be generated by the service provider computer 104 in order to identify information for a response to the prescription benefit check request 202. For example, the service provider computer 104 may determine that a pharmacy billing request can be generated in step 410. For example, during the processing of the prescription benefit check request 202, the service provider computer 104 may identify the network benefit check module 110 to identify the request type as a pharmacy billing request by Request type designation as "B".

At step 412, the service provider computer 104 may identify which pharmacy to populate in the pharmacy prescription request 204. In one non-limiting example, the pharmacy information utilized to populate the pharmacy prescription request 204 may be the pharmacy benefit information identified by the patient. For example, the patient may provide the healthcare provider with the patient's preferred pharmacy information. The patient's preferred pharmacy information may be included in the prescription benefit check request 202. During the processing the of the prescription benefit check request 202, the service provider computer 104 may identify the preferred pharmacy information in the prescription benefit check request 202. Alternatively, if no preferred pharmacy information is identified in the prescription benefit check request 202, a default pharmacy information may be populated in the pharmacy prescription request 204. Discussion regarding the determination of a default pharmacy may be found at least at FIGS. 7A and 7B herein.

At step 414, the service provider computer 104 may determine whether the identified pharmacy is a supported pharmacy within the system described in FIG. 1. For example, the service provider computer 104 may employ the network benefit check module 110 to access one or more supported pharmacy files 148. The network benefit check module 110 may compare a pharmacy identifier (e.g., a pharmacy name, pharmacy address, pharmacy identification number, etc.) to one or more tables within one or more supported pharmacy files 148 to determine if a match exists. The one or more tables may include fields including, without limitation, a pharmacy name, a pharmacy identification number, a pharmacy location (e.g., a postal code, an address including street address, city, state/province, and zip/postal code), etc.), and/or a support designation field including a support indicator (e.g., a "Y" for supported or a "N" for not supported). The service provider computer 104 may parse the one or more tables within the supported pharmacy files 148 to identify whether the pharmacy identifier exists in the one or more supported pharmacy files. If the pharmacy identifier exists in the one or more supported pharmacy files 148 (a match), and a "Y" support indicator accompanies the existing file, then the YES branch is followed and processing may proceed to step 418. If the pharmacy identifier does not exist in the one or more supported pharmacy files 148 (no match), and/or a "N" support indicator accompanies the existing file, then the NO branch is followed and processing may proceed to step 416.

At step 416, the service provider computer 104 may access one or more default pharmacy pricing files 150. The service provider computer 104 may employ a network benefit check module 110 to identify a medication identifier (e.g., a NDC identifier, an RxNorm medication identifier, or the like) submitted in the prescription benefit check request 202. The network benefit check module 110 may also access a prescribed quantity included in the prescription benefit check request 202. In one example, utilizing the NDC identifier and the prescribed quantity, the service provider computer 104 may parse the one or more default pharmacy pricing files 150 to determine a universal pharmacy price corresponding to the medication and prescribed quantity identified in the prescription benefit check request 202.

At step 418, the service provider computer 104 may access one or more pharmacy request files 146. In one non-limiting example, the service provider computer 104 may employ the network benefit check module 110 to access the one or more pharmacy request files 146. The one or more pharmacy request files 146 may be organized by a pharmacy identifier (e.g., a pharmacy name, a pharmacy identification number, etc.). Each of the pharmacy request files 146 may include a medication identifier, a quantity, and a specific price associated with the medication identifier and the quantity dispensed. The network benefit check module 110 may identify the medication identifier (e.g., an NDC identifier, an RxNorm medication identifier, or the like) submitted in the prescription benefit check request 202. The service provider 104 may also access a prescribed quantity included in the prescription benefit check request 202. In one example, utilizing the NDC identifier and the prescribed quantity, the service provider may parse the one or more pharmacy request files 146 to determine a specific pharmacy price corresponding to the medication and prescribed quantity identified in the prescription benefit check request 202.

At step 420, the service provider computer 104 may calculate the universal pharmacy pricing identified at step 416 or the specific pharmacy pricing identified at step 418. At step 422, the service provider computer 104 may format the pharmacy prescription request 204. In one non-limiting example, the prescription request 204 may include, without limitation, a request header, an insurance segment, a patient segment, a claim segment, a prescriber segment, and/or a pricing segment. For example, without limitation, the prescription request may include:

Request header
        BIN Number
        Version release number
        Request type code Processor control number
  Request count
  Pharmacy ID qualifier
  Pharmacy ID
  Date of Service
Insurance segment
  Segment identification
  Cardholder ID
  Group ID
  Person code
  Patient relationship code
Patient Segment
  Segment identification
  Patient first name
  Patient last name
  Date of birth
  Patient gender code
Claim segment
  Segment identification
  Prescription/Service reference number qualifier
  Prescription/Service reference number
  Product/Service Id qualifier
  Product/Service ID
  Quantity dispensed
  Fill number
  Days' supply
  Compound code
  Product selection code
  Date prescription written
  Quantity prescribed
Prescriber segment
  Segment identification
  Prescriber ID qualifier
  Prescriber ID
  Prescriber last name
Pricing segment
  Segment identification
  Ingredient cost submitted
  Dispensing fee submitted
  Flat sales tax amount submitted
  Percent sales tax amount submitted
  Usual and customary charge
  Gross amount due At step 426, the service provider computer 104 may deliver the pharmacy prescription request 204 to the pharmacy claims processor computer 106. At step 428, the service provider computer 104 awaits a response (e.g., a prescription response 206) from the pharmacy claims processor computer 106.

The method 400 may end after step 428.

Figure 5A:
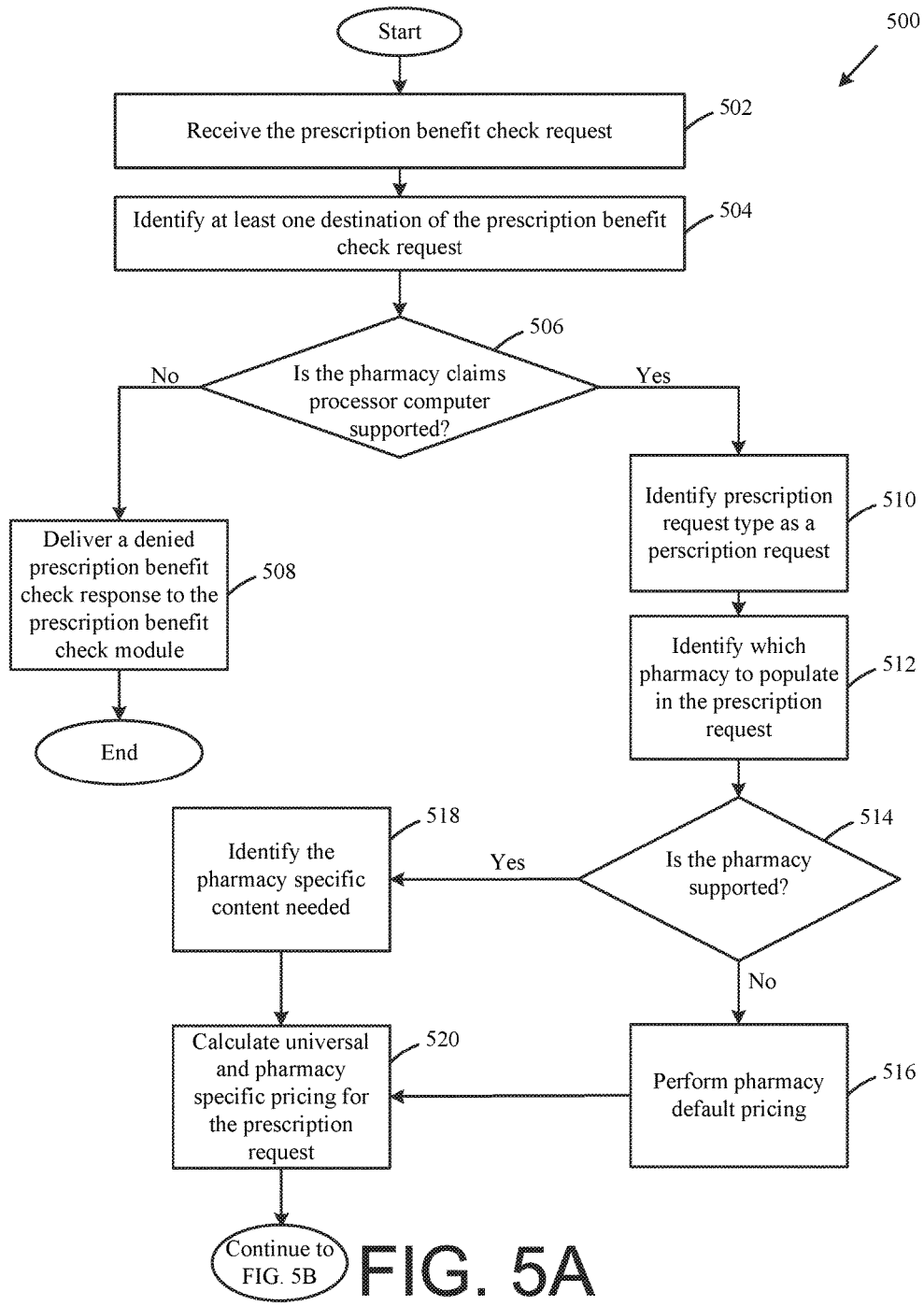
FIGS. 5A and 5B illustrate a flow chart of an example method for determining the request type of the prescription benefit check request as a billing request and processing the determined billing request, according to one exemplary embodiment.
Figure 5B:
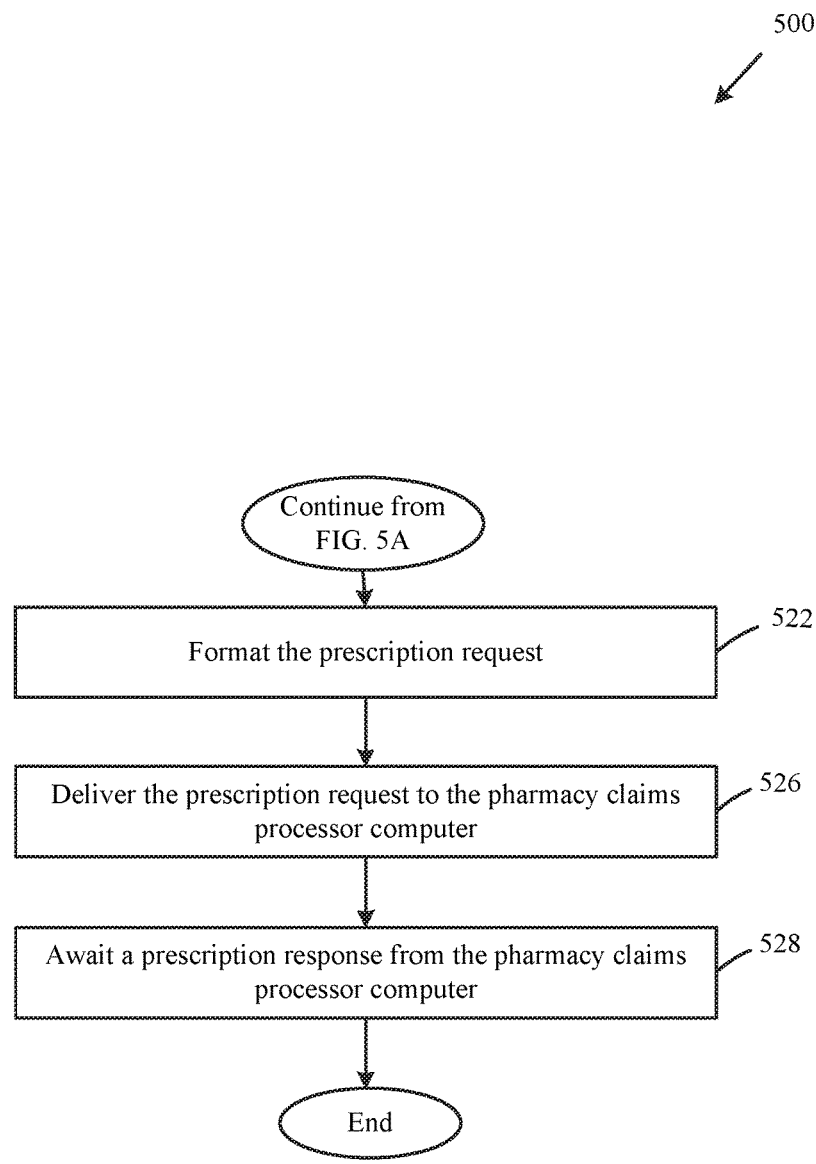

FIGS. 5A and 5B illustrate an example method 500 for determining the request type of the prescription benefit check request 202 as a billing request and processing the determined billing request. The block diagram 200 of FIG. 2 will be discussed in conjunction with the method 500. Referring now to FIGS. 1A, 1B, 2, 3A, 3B, 5A, and 5B the exemplary method 500 begins at the START step and continues to step 502, where the service provider computer 104 may receive the prescription benefit check request 202. At step 504, the service provider computer 104 may identify at least one destination of the prescription benefit check request 202. In one non-limiting example, the destination of the prescription benefit check request may be the pharmacy claims processor computer 106. The pharmacy claims processor computer 106 may be identified using the BIN Number or the BIN Number and Processor Control Number or the BIN Number and Group ID included in the prescription benefit check request 202.

At step 506, the service provider computer 104 may determine whether the identified pharmacy claims processor computer 106 is a supported pharmacy claims processor computer 106 within the system 100. In one non-limiting example, the service provider computer 104 may employ the network benefit check module 110 to access one or more supported pharmacy claims processor computer files 154 to determine whether the identified pharmacy claims processor computer 106 is a supported destination. For example, the network benefit check module 110 may access one or more supported pharmacy claims processor computer files 154. The network benefit check module 110 may compare the submitted BIN Number or the BIN Number and Processor Control Number or the BIN Number and Group ID to one or more tables within one or more supported pharmacy claims processor computer files 154 to determine if a match exists. The one or more tables may include, without limitation, a BIN Number field, a Processor Control Number field, a Group ID field, and/or a support designation field including a support indicator (e.g., a "Y" for supported or a "N" for not supported). The network benefit check module 110 may parse the one or more supported pharmacy claims processor files 154 to identify whether the BIN Number or the BIN Number and Processor Control Number or the BIN Number and Group ID exists (or is a match) in the one or more tables. If the BIN Number or the BIN Number and Processor Control Number or the BIN Number and Group ID exists (or is a match) in the one or more supported pharmacy claims processor computer files 154, and a "Y" support indicator accompanies the existing file, then the YES branch is followed and processing may proceed to step 510. If the BIN Number or the BIN Number and Processor Control Number or the BIN Number and Group ID does not exist in the one or more supported pharmacy claims processor computer files 154, and/or a "N" support indicator accompanies the existing file, then the NO branch is followed and processing may proceed to step 508.

At step 508, the service provider computer 104 may deliver a denied prescription benefit check response 208 to the healthcare provider device 102. The denied prescription benefit check response 208 can include a denial error code in a denial reason field of the denied prescription benefit check response 208 and optionally a further textual explanation of why the prescription benefit check request 202 was denied. The method 500 may end after step 508.

At step 510, the service provider computer 104 may determine the type and format of a prescription request to be generated by the service provider computer 104 in order to identify information for a response to the prescription benefit check request 202. For example, the service provider computer 104 may determine that a billing request can be generated in step 510. For example, during the processing of the prescription benefit check request 202, the service provider computer 104 may identify the request type as a billing request formatted under the NCPDP Telecom standard by a Request type designation "P1".

At step 512, the service provider computer 104 may identify which pharmacy to populate in the prescriber prescription request 204. In one non-limiting example, the pharmacy information utilized to populate the prescriber prescription request 204 may be the pharmacy benefit information identified by the patient. For example, the patient may provide the healthcare provider with the patient's preferred pharmacy information. The patient's preferred pharmacy information may be included in the prescription benefit check request 202. During the processing of the prescription benefit check request 202, the service provider computer 104 may identify the preferred pharmacy information in the prescription benefit check request 202. Alternatively, if no preferred pharmacy information is identified in the prescription benefit check request 202, a default pharmacy information may be populated in the pharmacy prescription request 204. Discussion regarding the determination of a default pharmacy may be found at least at FIGS. 7A and 7B herein.

At step 514, the service provider computer 104 may determine whether the identified pharmacy is a supported pharmacy within the system described in FIG. 1. For example, the service provider computer 104 may employ the network benefit check module 110 to access one or more supported pharmacy files 148. The network benefit check module 110 may compare a pharmacy identifier (e.g., a pharmacy name, pharmacy address, pharmacy identification number, etc.) to one or more tables within one or more supported pharmacy files 148 to determine if a match exists. The one or more tables may include fields including, without limitation, a pharmacy name, a pharmacy identification number, a pharmacy location (e.g., a postal code, an address (including street address, city, state/province, and zip/postal code), etc.), and/or a support designation field including a support indicator (e.g., a "Y" for supported or a "N" for not supported). The network benefit check module 110 may parse the one or more tables within the supported pharmacy files 148 to identify whether the pharmacy identifier exists (or is a match) in the one or more supported pharmacy files. If the pharmacy identifier exists in the one or more supported pharmacy files 148 (a match), and a "Y" support indicator accompanies the existing file, then the YES branch is followed and processing may proceed to step 518. If the pharmacy identifier does not exist in the one or more supported pharmacy files 148, and/or a "N" support indicator accompanies the existing file, then the NO branch is followed and processing may proceed to step 516.

At step 516, the service provider computer 104 may access one or more default pharmacy pricing files 150. The service provider computer 104 may employ the network benefit check module 110 to identify a medication identifier (e.g., NDC identifier, an RxNorm medication identifier, or the like) submitted in the prescription benefit check request 202. The service provider computer 104 may also access a prescribed quantity included in the prescription benefit check request 202. In one example, utilizing the NDC identifier and the prescribed quantity, the service provider may parse the one or more default pharmacy pricing files 150 to determine a universal pharmacy price corresponding to the medication and prescribed quantity identified in the prescription benefit check request 202.

At step 518, the service provider computer 104 may access one or more pharmacy request files 146. In one non-limiting example, the service provider 104 may employ the network benefit check module 110 to access the one or more pharmacy request files 146. The one or more pharmacy request files 146 may be organized by a pharmacy identifier (e.g., a pharmacy name, pharmacy address, pharmacy identification number, etc.). Each of the pharmacy request files 146 may include a medication identifier, a quantity, and a specific price associated with the medication identifier and the quantity dispensed. The network benefit check module 110 may identify the medication identifier (e.g., NDC identifier, an RxNorm medication identifier, or the like) submitted in the prescription benefit check request 202. The network benefit check module 110 may also access a prescribed quantity included in the prescription benefit check request 202. In one example, utilizing the NDC identifier and the prescribed quantity, the service provider may parse the one or more pharmacy request files 146 to determine a specific pharmacy price corresponding to the medication and prescribed quantity identified in the prescription benefit check request 202.

At step 520, the service provider computer 104 may calculate the universal pharmacy pricing identified at step 516 or the specific pharmacy pricing identified at step 518. At step 522, the service provider computer 104 may format the prescription request 204. In one non-limiting example, the prescription request 204 may include, without limitation, a request header, an insurance segment, a patient segment, a claim segment, a prescriber segment, and/or a pricing segment. For example, without limitation, the prescription request may include:

Request header
  BIN Number
  Version release number
  Request type code
  Processor control number
  Request count
  Pharmacy ID qualifier
  Pharmacy ID
  Date of Service
Insurance segment
  Segment identification
  Cardholder ID
  Group ID
  Person code
  Patient relationship code
Patient Segment
  Segment identification
  Patient first name
  Patient last name
  Date of birth
  Patient gender code
Claim segment
  Segment identification
  Prescription/Service reference number qualifier
  Prescription/Service reference number
  Product/Service Id qualifier
  Product/Service ID
  Quantity dispensed
  Fill number
  Days' supply
  Compound code
  Product selection code
  Date prescription written
  Quantity prescribed
Prescriber segment
  Segment identification
  Prescriber ID qualifier
  Prescriber ID
  Prescriber last name
Pricing segment
  Segment identification
  Ingredient cost submitted
  Dispensing fee submitted
  Flat sales tax amount submitted
  Percent sales tax amount submitted
  Usual and customary charge
  Gross amount due At step 526, the service provider computer 104 may deliver the prescriber prescription request 204 to the pharmacy claims processor computer 106. At step 528, the service provider computer 104 awaits a response (e.g., a prescription response 206) from the pharmacy claims processor computer 106.

The method 500 may end after step 528.

Figure 6:
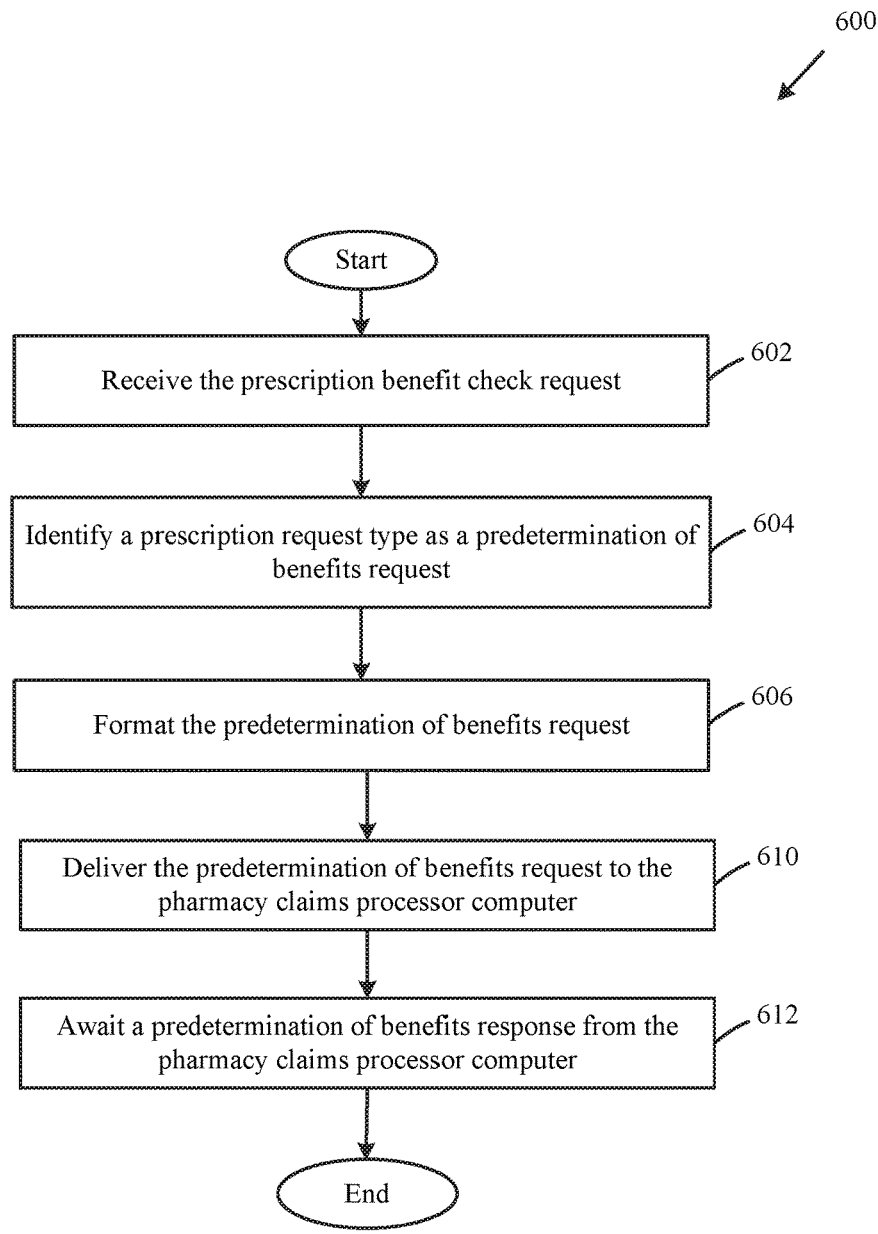
FIG. 6 illustrates a flow chart of an example method for determining the request type of the prescription benefit check request as a predetermination of benefits request and processing the determined predetermination of benefits request, according to one exemplary embodiment.

FIG. 6 illustrates an example method 600 for determining the request type of the prescription benefit check request 202 as a predetermination of benefits request and processing the determined predetermination of benefits request. The block diagram 200 of FIG. 2 will be discussed in conjunction with the method 600. Referring now to FIGS. 1A, 1B, 2, 3A, 3B and 6, the exemplary method 600 begins at the START step and continues to step 602, where the service provider computer 104 may receive the prescription benefit check request 202. At step 604, the service provider computer 104 may identify the request type associated with the prescription benefit check request 202. For example, without limitation, the prescription benefit check request 202 may be associated with a pharmacy billing request, a billing request, or a predetermination of benefits request. During the processing of the prescription benefit check request 202, the service provider computer 104 may identify the request type based upon the request type designation included in the prescription benefit check request 202 (e.g., as a billing request by a Request type designation "P1", as a pharmacy billing request by a Request type designation "B1", or as a predetermination of benefits request by a Request type designation "D1"). As illustrated in FIG. 6, the request type designation included in exemplary method 600 is a predetermination of benefits request type (e.g., a Request type designation "D1" is identified).

At step 606, the service provider computer 104 may format the predetermination of benefits prescription request 204. In one non-limiting example, the predetermination of benefits prescription request 204 may include, without limitation, a request header, an insurance segment, a patient segment, a claim segment, a prescriber segment, and/or a pricing segment. For example, without limitation, the predetermination of benefits prescription request 204 may include:

- Request header
  - BIN Number
  - Version release number
  - Request code
  - Processor control number
  - Request count
  - Pharmacy ID qualifier
  - Pharmacy ID
  - Date of Service
- Insurance segment
  - Segment identification
  - Cardholder ID
  - Group ID
  - Person code
  - Patient relationship code
- Patient Segment
  - Segment identification
  - Patient first name
  - Patient last name
  - Date of birth
  - Patient gender code
- Claim segment
  - Segment identification
  - Prescription/Service reference number qualifier
  - Prescription/Service reference number
  - Product/Service Id qualifier
  - Product/Service ID
  - Quantity dispensed
  - Fill number
  - Days' supply
  - Compound code
  - Product selection code
  - Date prescription written
  - Quantity prescribed
- Prescriber segment
  - Segment identification
  - Prescriber ID qualifier
  - Prescriber ID
  - Prescriber last name
- Pricing segment
  - Segment identification
  - Ingredient cost submitted
  - Dispensing fee submitted
  - Flat sales tax amount submitted
  - Percent sales tax amount submitted
  - Usual and customary charge
  - Gross amount due At step 610, the service provider computer 104 may deliver the predetermination of benefits prescription request 204 to the pharmacy claims processor computer 106. At step 612, the service provider computer 104 awaits a response (e.g., a prescription response 206) from the pharmacy claims processor computer 106. The method 600 may end after step 612.

Figure 7A:
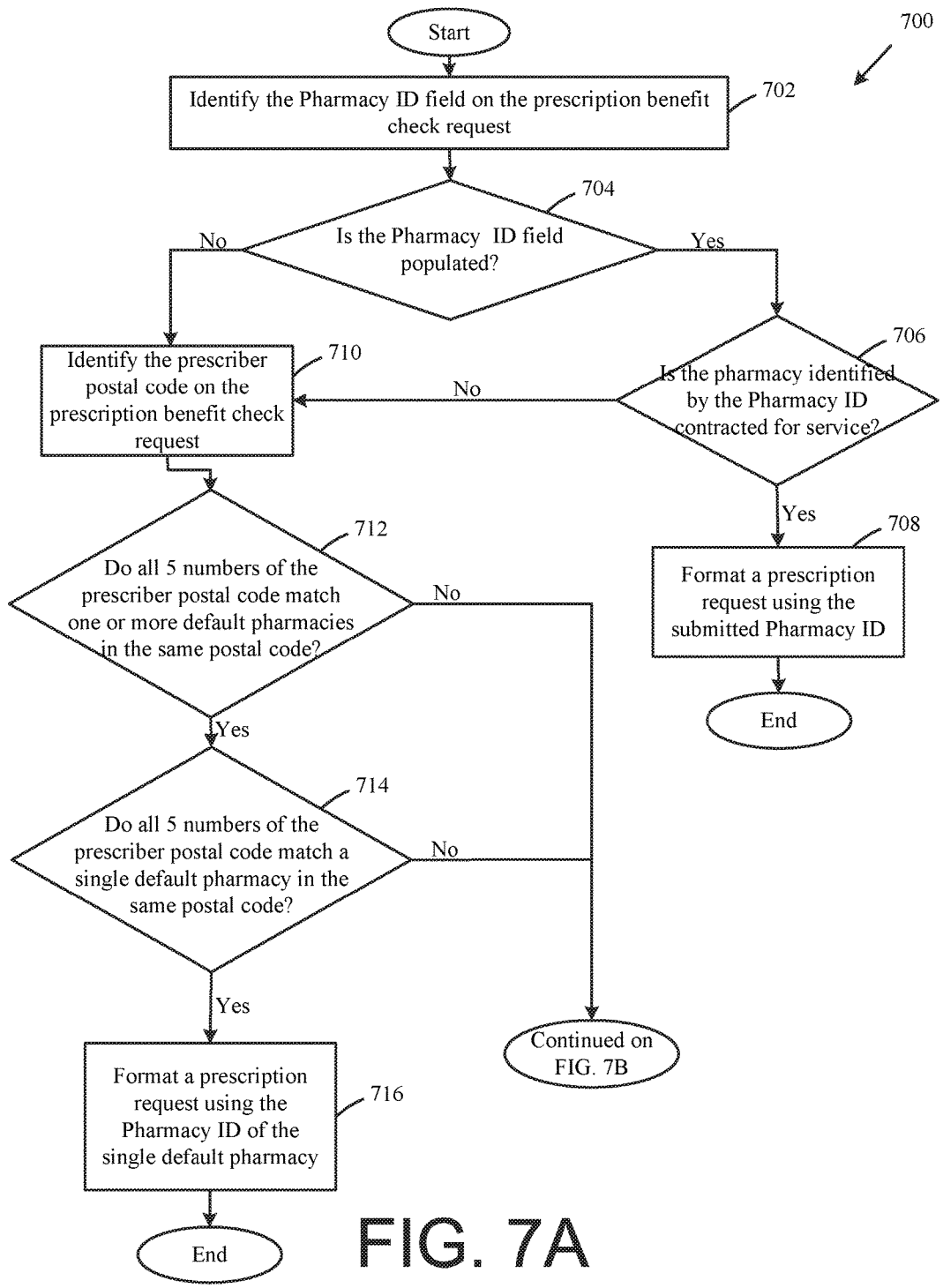
FIGS. 7A and 7B illustrate a flow chart of an example method for determining a default pharmacy associated with the prescription benefit check request, according to one exemplary embodiment.
Figure 7B:
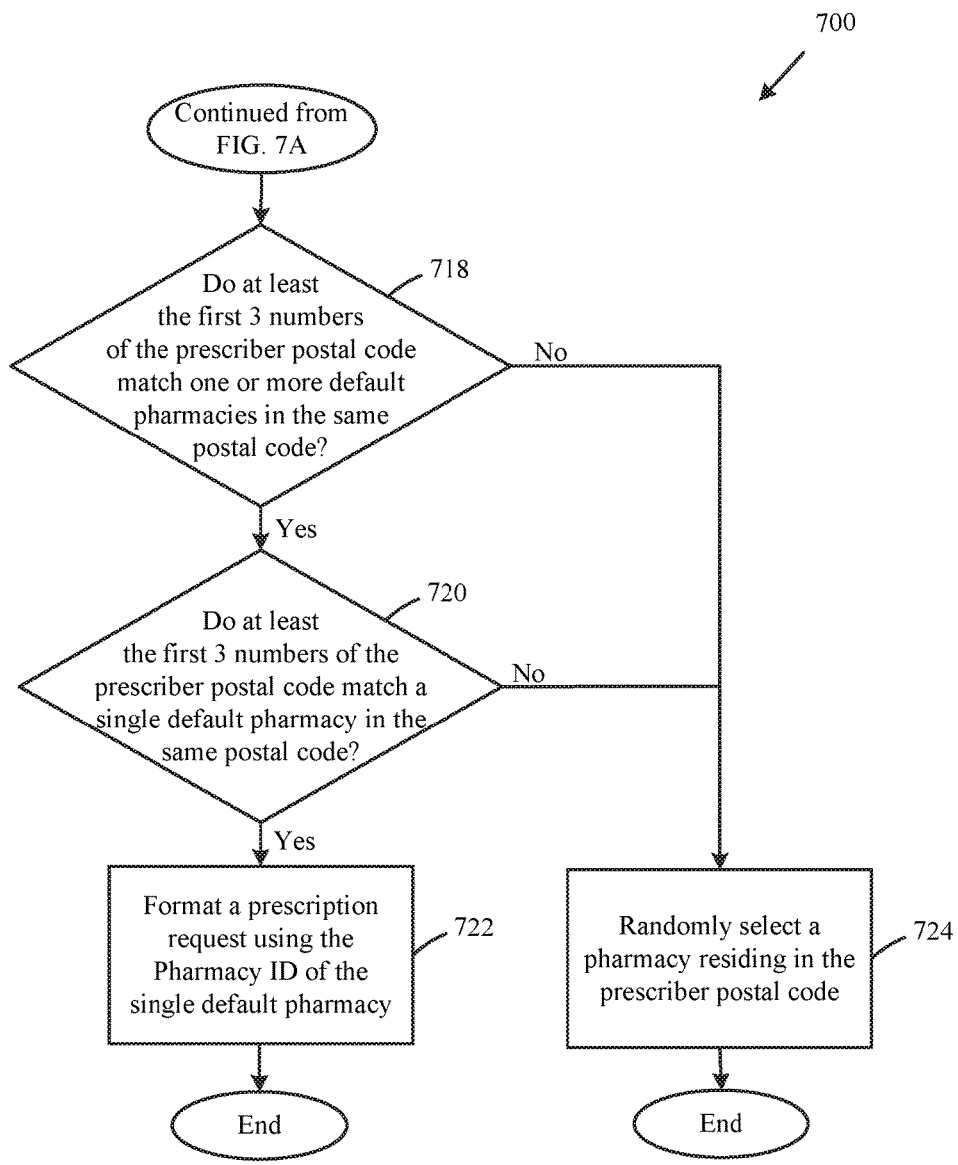

FIGS. 7A and 7B illustrate an example method 700 for determining a default pharmacy associated with the prescription benefit check request 202. The block diagram 200 of FIG. 2 will be discussed in conjunction with the method 700. Referring now to FIGS. 1A, 1B, 2, 3A, 3B, 7A, and 7B, the exemplary method 700 begins at the START step and continues to step 702, where the service provider computer 104 may identify the pharmacy ID field in the submitted prescription benefit check request 202. At step 704, the service provider computer 104 may determine whether the pharmacy ID field in the submitted prescription benefit check request 202 is populated. In one example implementation, the pharmacy ID corresponds to the patient's preferred pharmacy. If the pharmacy ID field is populated, then the YES branch is followed and processing may proceed to step 706. If the pharmacy ID field is not populated, then the NO branch is followed and processing may proceed to step 710.

At step 706, the service provider computer 104 may determine whether the pharmacy associated with the pharmacy ID is a contracted pharmacy. For example, the service provider computer 104 may employ the network benefit check module 110 to access one or more supported pharmacy files 148. The network benefit check module 110 may compare the pharmacy ID (e.g., a pharmacy name, pharmacy address, pharmacy identification number, etc.) to one or more tables within one or more supported pharmacy files 148 to determine if a match exists. The one or more tables may include, without limitation, a pharmacy name field, a pharmacy identification number field, a pharmacy location field (e.g., a postal code, an address (including street address, city, state/province, and zip/postal code), etc.), a support designation field including a support indicator (e.g., a "Y" for supported or a "N" for not supported), and/or a default pharmacy status indicator (i.e., "DF"). The network benefit check module 110 may parse the one or more tables within the supported pharmacy files 148 to identify whether the pharmacy ID exists (or is a match) in the one or more supported pharmacy files. If the pharmacy ID exists (or is a match) in the one or more supported pharmacy files 148, and a "Y" support indicator accompanies the existing file, then the YES branch is followed and processing may proceed to step 708. If the pharmacy ID does not exist (is not a match) in the one or more supported pharmacy files 148, and/or a "N" support indicator accompanies the existing file, then the NO branch is followed and processing may proceed to step 710.

At step 708, the service provider computer 104 may format the prescription request 204 to a corresponding request type. For example, the request type may include, without limitation, a pharmacy billing request (e.g., request type "B1"), a billing request (e.g., request type "P1"), or a predetermination of benefits request (e.g., request type "D1"). The method 700 may end after step 708.

At step 710, the service provider computer 104 may identify the prescriber postal code submitted in the prescription benefit check request 202. In one non-limiting example, the service provider computer 104 may employ the network benefit check module 110 to parse the prescription benefit check request 202 to identify the prescriber postal code field. The network benefit check module 110 may identify the numbers populated in the prescriber postal code field. For example, the network benefit check module 110 may identify the five numbers of the prescriber postal code to be 99026.

At step 712, the service provider computer 104 may determine whether the identified prescriber postal code matches one or more default pharmacies within the same identified postal code. In one non-limiting example, the service provider computer 104 may employ the network benefit check module 110 to identify one or more default pharmacies that match all five numbers of the identified prescriber postal code. For example, if the identified prescriber postal code is 99026, the network benefit check module 110 may determine one or more default pharmacies within the postal code 99026. For example, the network benefit check module 110 may compare the identified prescriber postal code (e.g., 99026) with one or more default pharmacies in one or more supported pharmacy files 148 to determine if a match exists. The network benefit check module 110 may parse the one or more tables within the supported pharmacy files 148 to identify whether the pharmacies within a postal code include the default designation "DF". If the network benefit module 110 identifies one or more default pharmacies associated with the all five numbers of the identified prescriber postal code (a match), then the YES branch is followed and processing may proceed to step 714. If the network benefit module 110 does not identify one or more default pharmacies associated with the all five numbers of the identified prescriber postal code (no match), then the NO branch is followed and processing may proceed to step 718.

At step 714, the service provider computer 104 may employ the network benefit module 110 to determine whether the identified prescriber postal code matches a single pharmacy within the same identified postal code. If the network benefit module 110 identifies a single default pharmacy associated with the all five numbers of the identified prescriber postal code (a match), then the YES branch is followed and processing may proceed to step 716. If the network benefit module 110 does not identify a default pharmacy associated with the all five numbers of the identified prescriber postal code (no match), then the NO branch is followed and processing may proceed to step 718.

At step 716, the service provider computer 104 may format the prescription request 204 to a corresponding request type and include the identified pharmacy ID associated with a default pharmacy. The method 700 may end after step 716.

At step 718, the service provider computer 104 may determine whether at least the first 3 numbers of the identified prescriber postal code matches one or more default pharmacies within the same identified postal code. In one non-limiting example, the service provider computer 104 may employ the network benefit module 110 to identify one or more default pharmacies that match at least the first 3 numbers of the identified prescriber postal code. For example, if the identified prescriber postal code is 99026, the network benefit module 110 may determine one or more default pharmacies within the postal code 99026 by searching for at least 990 in the first three numbers of the postal code. For example, the service provider computer 104 may compare the identified prescriber postal code (i.e., 99026) with one or more default pharmacies in one or more supported pharmacy files 148 with the designation "DF" to determine if a match exists. The one or more supported pharmacy files 148 may be organized by postal code. If the network benefit module 110 identifies one or more default pharmacies associated with the at least the first three numbers of the identified prescriber postal code (a match), then the YES branch is followed and processing may proceed to step 720. If the network benefit module 110 does not identify one or more default pharmacies associated with at least the first three numbers of the identified prescriber postal code (no match), then the NO branch is followed and processing may proceed to step 724.

At step 720, the service provider computer 104 may employ the network benefit module 110 to determine whether the identified prescriber postal code matches a single pharmacy the same first three numbers of the identified postal code. If the network benefit module 110 identifies a single default pharmacy associated with the first three numbers of the identified prescriber postal code (a match), then the YES branch is followed and processing may proceed to step 722. If the network benefit module 110 does not identify a default pharmacy associated with the first three numbers of the identified prescriber postal code (no match), then the NO branch is followed and processing may proceed to step 724.

At step 722, the service provider computer 104 may format the prescription request 204 to a corresponding request type and including the identified pharmacy ID associated with the default pharmacy. The method 700 may end after step 722.

At step 724, the service provider computer 104 may randomly select a pharmacy within the prescriber postal code. The service provider computer 104 may format the prescription request 204 to a corresponding request type and include the identified pharmacy ID associated with the randomly selected pharmacy. The method 700 may end after step 724.

Figure 8:
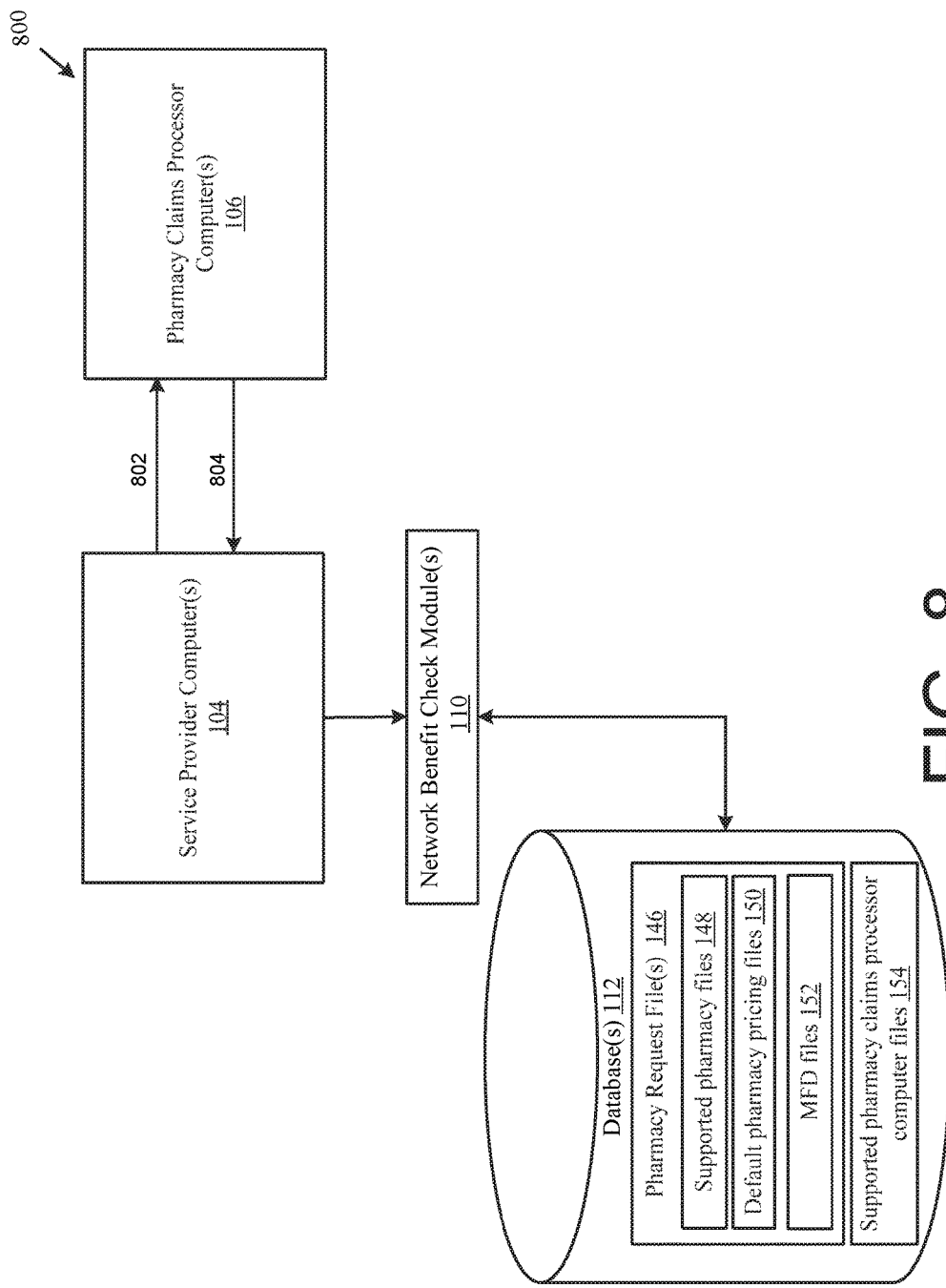
FIG. 8 is a block diagram for receiving and communicating a reversal request, according to one exemplary embodiment.
Figure 9:
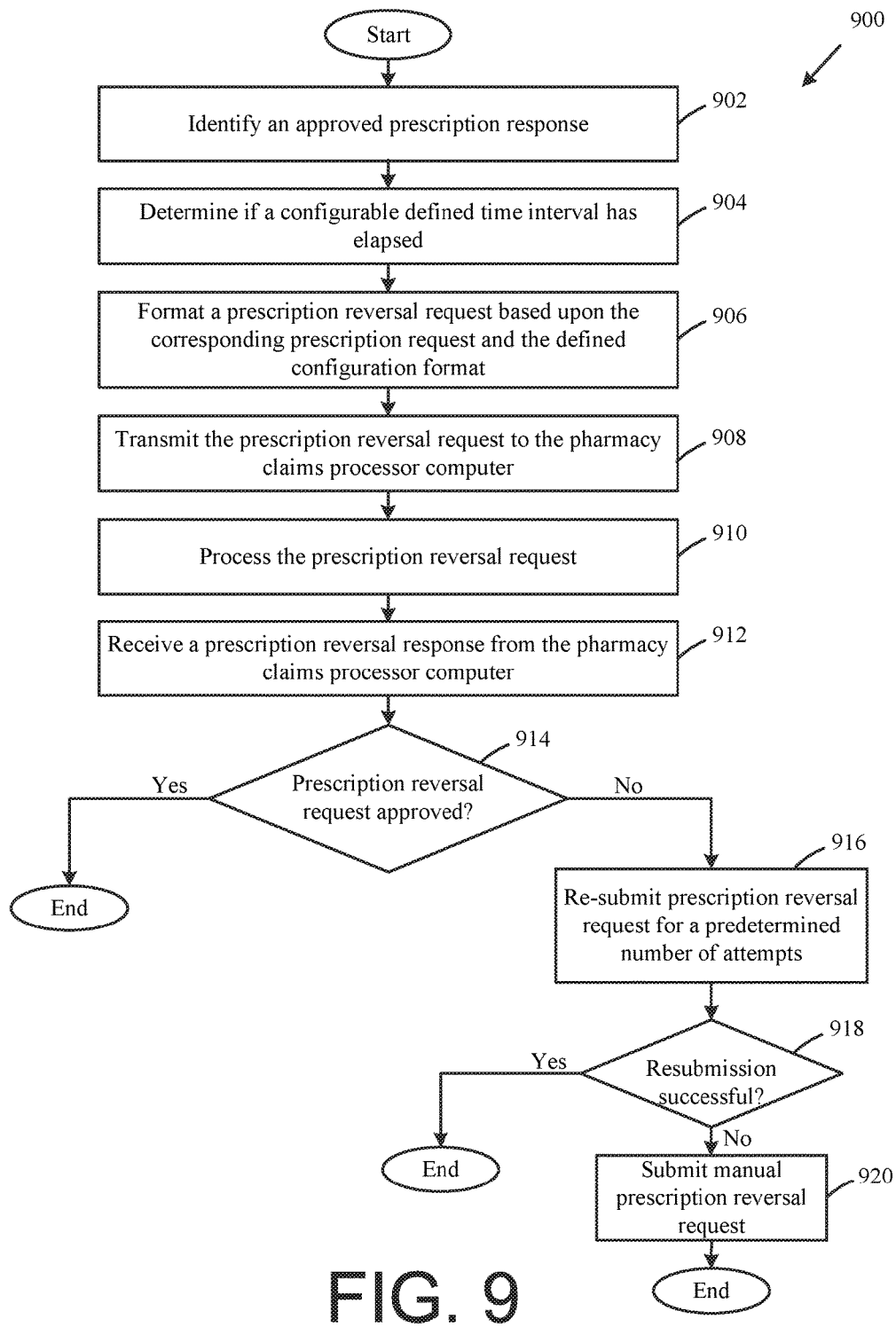
FIG. 9 illustrates a flow chart of an example method for receiving and communicating a reversal request, according to one exemplary embodiment.

FIG. 8 illustrates an example block diagram 800 for receiving and communicating a reversal request according to an example embodiment of the disclosure. FIG. 9 illustrates an example method 900 for receiving and communicating a reversal request, according to an example embodiment of the disclosure. The block diagram 800 of FIG. 8 will be discussed in conjunction with the method of 900 of FIG. 9. Referring now to FIGS. 1A, 1B, 2, 8, and 9, the exemplary method 900 begins at the START step and continues to step 902, where the service provider computer 104 may identify whether the prescription request 204 was approved. In one non-limiting example, the service provider computer 104 may determine whether the prescription request 204 was approved by identifying the response status field in the prescription response 206. If the response status field is populated with a "P" (or a number of other response status indicators known to those of ordinary skill in the art), then the prescription request 204 was approved. If the response status field is populated with an "R" (or a number of other response status indicators known to those of ordinary skill in the art), then the prescription request 204 was denied. By way of example, FIG. 9 applies to both the pharmacy billing request (e.g., request type "B1") and the billing request (e.g., request type "P1").

At step 904, the service provider computer 104 may determine whether a predetermined configurable defined time interval has elapsed since the prescription response 206 or the denied prescription benefit check response 208 was transmitted to the healthcare provider device 102. The predetermined configurable defined time interval may be any suitable time interval such as 30 seconds, 2 minutes, 5 minutes, or the like. The predetermined configurable defined time interval may be any suitable time range between 1 second and 60 minutes.

At step 906, the service provider computer 104 may format a reversal request 802 based at least in part upon the corresponding request type (e.g., pharmacy or prescriber) and the corresponding defined format described herein. At step 908, the service provider computer 104 may transmit the reversal request 802 to the pharmacy claims processor computer 106. In one non-limiting example, the pharmacy claims processor computer 106 is the same benefits computer the corresponding prescription request 204 was previously submitted to. At step 910, the pharmacy claims processor computer 106 may process the reversal request 802 and at step 912 the service provider computer 104 may receive a reversal response 804 from the pharmacy claims processor computer 106.

At step 914, the service provider computer 104 may determine whether the reversal request 802 was approved. If the reversal request 802 was approved, then the YES branch is followed and the method 900 may end. If the reversal request 802 was not approved, then the NO branch is followed and processing may proceed to step 916.

At step 916, the service provider computer 104 may resubmit the reversal request 802 to the pharmacy claims processor computer 106. The reversal request 802 may be resubmitted to the pharmacy claims processor computer 106 for a predetermined configurable number of attempts. For example, service provider computer 104 may attempt to resubmit the reversal request 802 to the pharmacy claims processor computer 106, 2 times, 3 times, or any suitable number of attempts.

At step 918, the service provider computer 104 may determine whether the resubmission of the reversal request 802 was successful. If the resubmission of the reversal request 802 was approved, then the YES branch is followed and the method 900 may end. If the resubmission of the reversal request 802 was not approved, then the NO branch is followed and processing may proceed to step 920. At step 920, the service provider computer may submit a manual reversal request 802 to the pharmacy claims processor computer 106. The method 900 may end after step 920.

Figure 10:
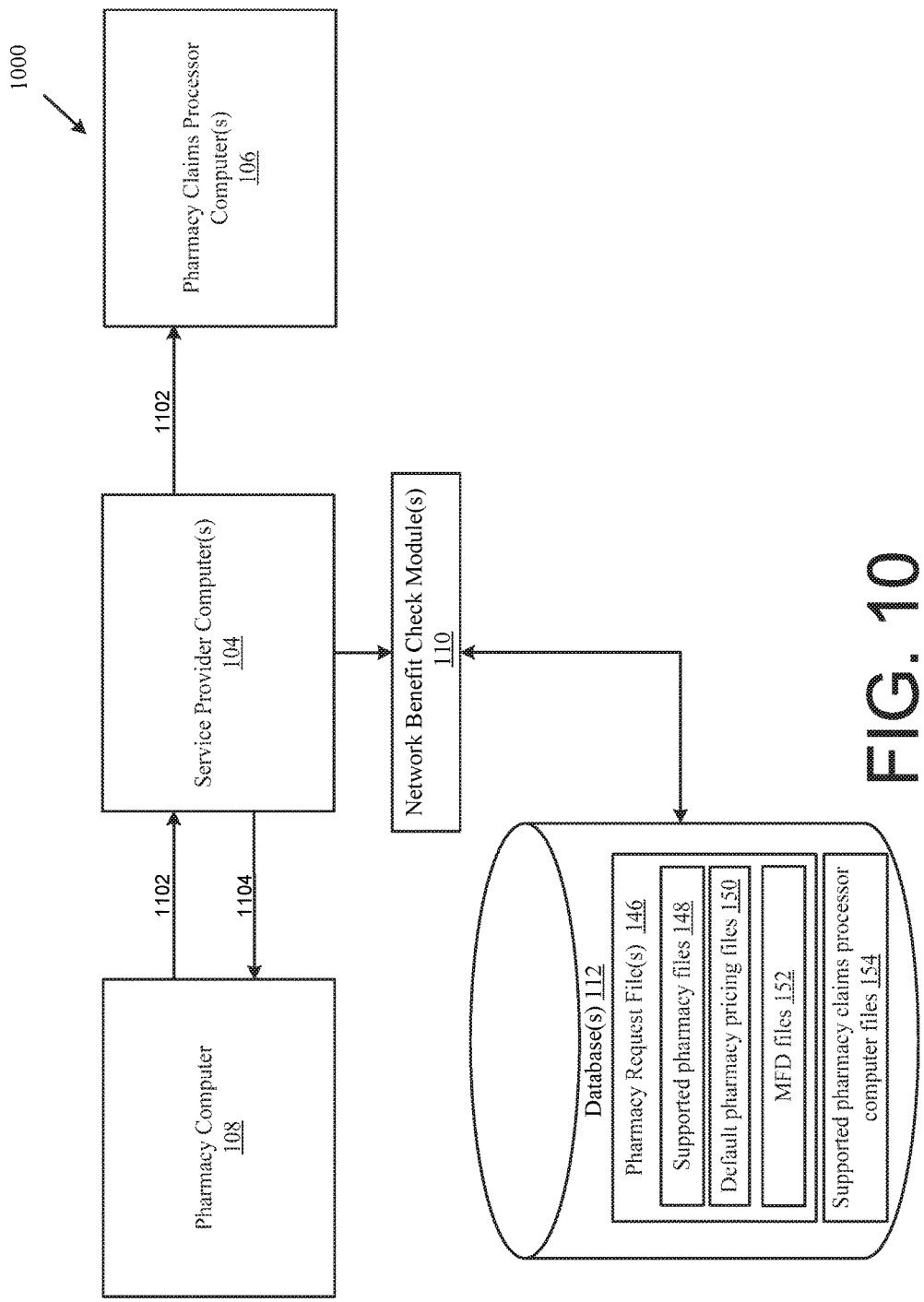
FIG. 10 is a block diagram for capturing pharmacy specific data, according to one exemplary embodiment.
Figure 11A:
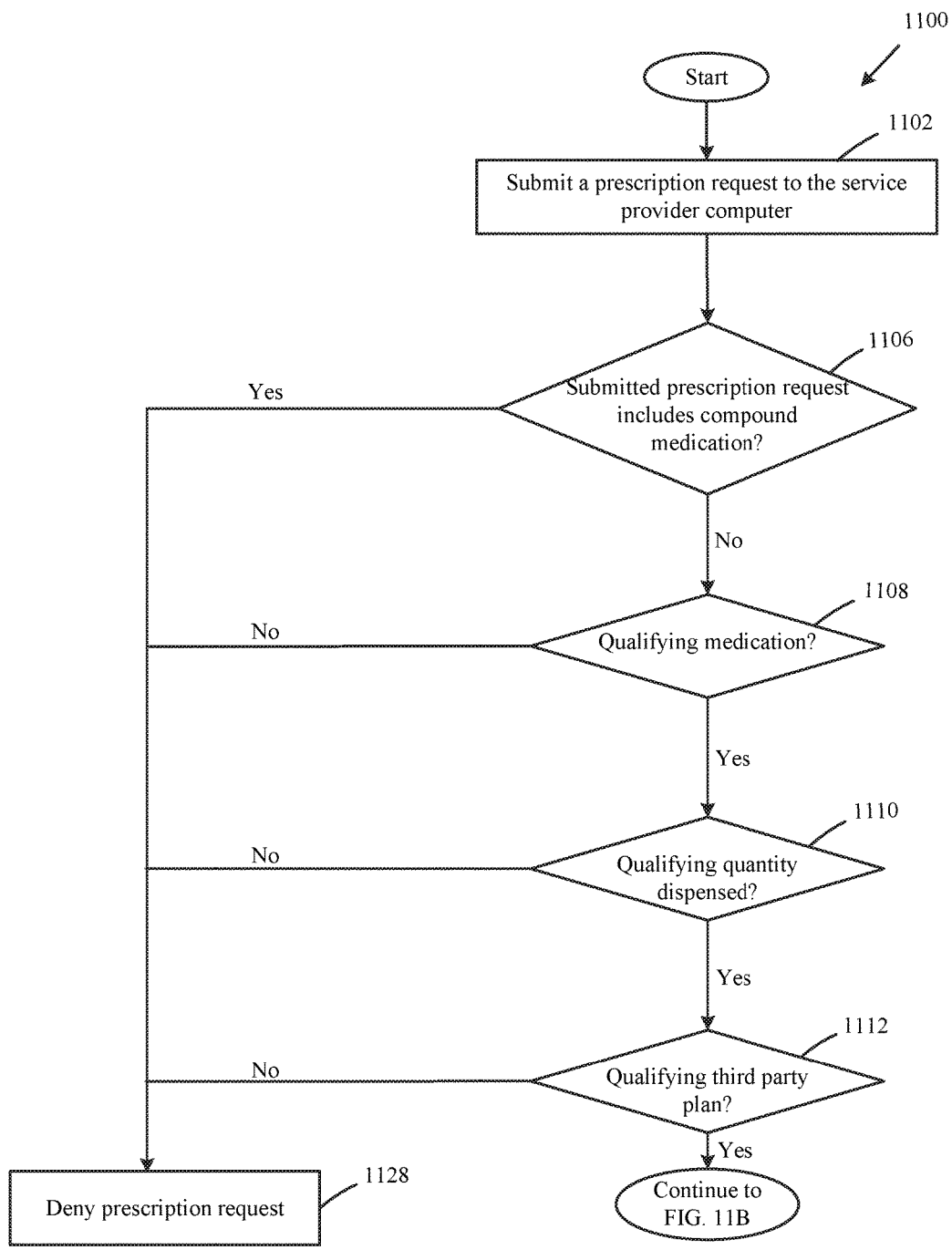
FIGS. 11A and 11B illustrates a flow chart of an example method for capturing pharmacy specific data, according to one exemplary embodiment.
Figure 11B:
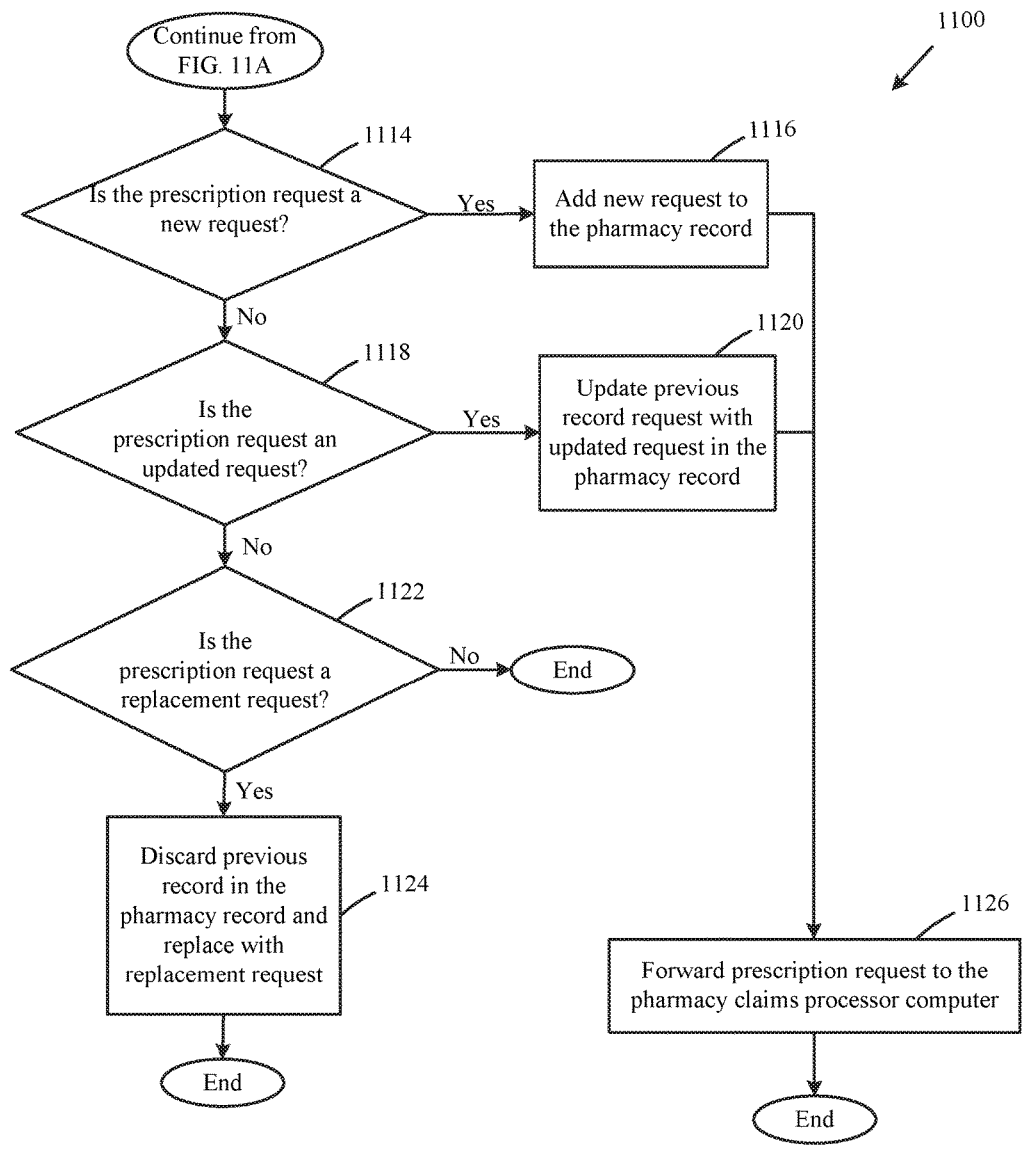

FIG. 10 illustrates an example block diagram 1000 for capturing pharmacy specific data according to an example embodiment of the disclosure. FIGS. 11A and 11B illustrate an example method 1100 for capturing pharmacy specific data, according to an example embodiment of the disclosure. The block diagram 1000 of FIG. 10 will be discussed in conjunction with the method of 1100 of FIGS. 11A and 11B. Referring now to FIGS. 1A, 1B, 10, 11A, and 11B, the exemplary method 1100 begins at the START step and continues to step 1102, where the service provider computer 104 may receive a prescription request 1002 from a pharmacy computer 108.

At step 1106, the service provider computer 104 may determine whether the submitted prescription request 1002 includes a compound medication. In one non-limiting example, the determination may be based upon a value in the Compound Code field included in the prescription request 1002. If the compound code value indicates a compound medication, then the YES branch is followed and processing may proceed to step 1128. If the compound code value does not indicate a compound medication, then the NO branch is followed and processing may proceed to step 1108.

At step 1108, the service provider computer 104 may determine whether the prescription request 1002 is for a qualifying medication. For example, the service provider computer 104 may employ the network benefit check module 110 to compare the medication identifier (e.g., NDC, RxNorm medication identifiers, or the like) to data included in one or more MFD files 152 to determine if a match exists. In one non-limiting example, the one or more MFD files 152 may include, one or more fields including a most frequently dispensed medication (MFD) identifier field (e.g., MFD: NDC field). If the medication qualifies (a match), then the YES branch is followed and processing may proceed to step 1110. If the medication does not qualify (no match), then the NO branch is followed and processing may proceed to step 1128.

At step 1110, the service provider computer 104 may determine whether the prescription request 1002 is for a qualifying quantity prescribed to be dispensed. For example, the service provider computer 104 may employ the network benefit check module 110 to compare the quantity prescribed to be dispensed (submitted in the prescription request 1002) to data included in one or more MFD files 152 to determine if a match exists. In one non-limiting example, the one or more MFD files 152 may include, one or more fields including a most frequently dispensed medication quantity dispensed field (e.g., MFD:quantity dispensed field), and/or a most frequently dispensed medication days' supply dispensed field (e.g., MFD:days' supply dispensed field). If the quantity prescribed qualifies (a match exists), then the YES branch is followed and processing may proceed to step 1112. If the medication and the quantity prescribed do not qualify (no match exists), then the NO branch is followed and processing may proceed to step 1128.

At step 1112, the service provider computer 104 may determine whether the prescription request 1002 is associated with a pharmacy claims processor computer 106. In one non-limiting example, the service provider computer 104 may compare the BIN Number or the BIN Number and Processor Control Number or the BIN Number and Group ID submitted in the prescription request 1002 with one or more supported pharmacy claims processor computer files 154 in database 112 to determine if a match exists. The one or more supported pharmacy claims processor computer files 154 may include, without limitation a list of one or more pharmacy claims processor computers 106. If the submitted pharmacy claims processor computer does not match an excluded pharmacy claims processor computer in the one or more supported pharmacy claims processor computer files 154, the submitted pharmacy claims processor computer is a qualifying pharmacy claims processor computer and the YES branch is followed and processing may proceed to step 1114. If the submitted pharmacy claims processor computer matches an excluded pharmacy claims processor computer in the one or more supported pharmacy claims processor computer files 154, then the NO branch is followed and processing may proceed to step 1128.

At step 1114, the service provider computer 104 may determine whether the prescription request 1002 is a new request. For example, if the prescription request 1002 is for a medication and/or quantity dispensed that does not exist in the pharmacy request files 146, the prescription request 1002 is designated as a new request. If the prescription request is a new request, the YES branch is followed and processing may proceed to step 1116. If the prescription request is not a new request, the NO branch is followed and processing may proceed to step 1118.

At step 1116, the service provider computer may create a new record in the pharmacy request files 146. The new record may include, without limitation, the contracted pharmacy information, the medication information, cost information, and/or the quantity dispensed information. At step 1118, the service provider computer 104 may determine whether the prescription request 1002 is an updated request. For example, if the prescription request 1002 is from a contracted pharmacy for a medication and/or quantity dispensed that includes updated information in a record in the pharmacy request files 146, the prescription request 1002 is designated as an updated request. If the prescription request 1002 is an updated request, the YES branch is followed and processing may proceed to step 1120. If the prescription request is not an updated request, the NO branch is followed and processing may proceed to step 1122.

At step 1120, the service provider computer may update the record in the pharmacy request files 146. The updated record may include, without limitation, the contracted pharmacy information (e.g., NPI code, DEA number, state license number, NCPDP provider ID, pharmacy identification qualifier, pharmacy identification, store and/or chain name, or the like), the medication information (e.g., medication name(s), NDC number(s), cost information, and/or the quantity dispensed information. At step 1122, the service provider computer 104 may determine whether the prescription request 1002 is a replacement request. For example, if the prescription request 1002 is from a contracted pharmacy for a medication and/or quantity dispensed that includes replacement information for a record in the pharmacy request files 146, the prescription request 1002 is designated as a replacement request. If the prescription request is a replacement request, the YES branch is followed and processing may proceed to step 1124. If the prescription request is not a replacement request, the NO branch is followed and processing may end.

At step 1124, the service provider computer may discard the previous record in the pharmacy request files 146 and replace the record with the replacement request. The replacement record may include, without limitation, the contracted pharmacy information, the medication information, cost information, and/or the quantity dispensed information. The method 1100 may end after step 1124.

At step 1126, if the prescription request 1102 is designated as a new request or an updated request, the service provider computer may forward the prescription request 1002 to the pharmacy claims processor computer 106. The method 1100 may end after step 1126.

At step 1128, the service provider may generate a denial of the prescription request 1002 and a denied prescription request 1004 may be delivered back to the pharmacy computer 108. The method 1100 may end after step 1128.

Various block and/or flow diagrams of systems, methods, apparatus, and/or computer program products according to example embodiments of the disclosure are described above. It will be understood that one or more blocks of the block diagrams and steps of the flow diagrams, and combinations of blocks in the block diagrams and combinations of steps in the flow diagrams, respectively, can be implemented by computer-executable program instructions. Likewise, some blocks of the block diagrams and steps of the flow diagrams may not necessarily need to be performed in the order presented, or may not necessarily need to be performed at all, according to some embodiments.

These computer-executable program instructions may be loaded onto a special-purpose service provider computer to produce a particular machine, such that the instructions that execute on the computer, processor, or other programmable data processing apparatus create means for implementing one or more functions specified in the flow diagram step or steps. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram step or steps. As an example, various embodiments of the disclosure may provide for a computer program product including a computer-usable medium having a computer-readable program code or program instructions embodied therein, said computer-readable program code adapted to be executed to implement one or more functions specified in the flow diagram step or steps. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram step or steps.

Accordingly, blocks of the block diagrams and steps of the flow diagrams support combinations of means for performing the specified functions, combinations of elements or steps for performing the specified functions, and program instruction means for performing the specified functions. It will also be understood that each block of the block diagrams and step of the flow diagrams, and combinations of blocks in the block diagrams and steps of the flow diagrams, can be implemented by the special-purpose service provider computer system that performs the specified functions, elements, or steps.

Many modifications and other embodiments of the disclosure set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A computer-implemented method for determining and communicating benefit coverage information, the method comprising:

receiving, by one or more service provider computers comprising one or more processors and originating from a healthcare provider computer associated with a prescriber, a prescription benefit check request comprising at least one or more patient data identifying a patient, one or more patient pharmacy benefit data, an identifier for a prescribed medication, and one or more of prescriber data identifying the prescriber;

accessing, by the one or more service provider computers, a database or data storage device storing one or more pharmacy request files comprising pharmacy information captured from a previously submitted pharmacy requests, the one or more pharmacy request files including at least a most frequently dispensed National Drug Code (NDC) number, a quantity dispensed associated with the preceding NDC Number, and a usual & customary charge;

determining, by the one or more service provider computers, a pharmacy request file corresponding to patient pharmacy benefit data from the one or more pharmacy request files;

accessing, by the one or more service provider computers, the pharmacy request file to determine a most frequently dispensed NDC number, a quantity dispensed associated with the preceding NDC number, and a usual & customary charge corresponding to the identifier for the prescribed medication;

formatting, by the one or more service provider computers, a prescription request including at least the accessed most frequently dispensed NDC number, quantity dispensed associated with the preceding NDC number, and usual & customary charge corresponding to the identifier for the prescribed medication, the one or more patient data, and the one or more prescriber data included in the prescription benefit check request;

transmitting, by the one or more service provider computers, the prescription request to a pharmacy claims processor computer for processing;

receiving, by the one or more service provider computers from the pharmacy claims processor computer, a prescription response corresponding to the processed prescription request;

capturing, by the one or more service provider computers, information from the prescription response;

generating, by the one or more service provider computers, a prescription benefit check response;

inserting, by the one or more service provider computers, at least a portion of the information from the prescription response into the prescription benefit check response;

transmitting, by the one or more service provider computers, the prescription benefit check response to the healthcare provider computer;

identifying, by the one or more service provider computers, whether the prescription request is approved;

determining, by the one or more service provider computers, whether a predetermined time interval has elapsed since the prescription benefit check response was transmitted to the healthcare provider computer;

formatting, by the one or more service provider computers, a reversal request based at least in part upon a request type of the prescription benefit check request; and transmitting, by the one or more service provider computers, the reversal request to the pharmacy claims processor computer.

2. The computer-implemented method of claim 1, further comprising determining, by the one or more service provider computers, a pharmacy claims processor computer to transmit the prescription request to, wherein the determination is based at least in part on one or more pharmacy claims processor computer identifiers submitted within the prescription benefit check request.

3. The computer-implemented method of claim 2, wherein the one or more pharmacy claims processor computer identifiers includes at least one of (i) a Banking Identification Number (BIN Number), (ii) the BIN Number and a Processor Control Number, or (iii) the BIN Number and a Group ID.

4. The computer-implemented method of claim 1, wherein determining, by the one or more service provider computers, a pharmacy request file corresponding to a patient pharmacy benefit data from the one or more pharmacy request files comprises:

determining, by the one or more service provider computers, whether the patient pharmacy benefit data includes a pharmacy identifier corresponding to a pharmacy, wherein:

if the patient pharmacy benefit data does include a pharmacy identifier corresponding to a pharmacy, determining, by the one or more service provider computers, the pharmacy request file based at least upon the pharmacy identifier, or if the patient pharmacy benefit data does not include a pharmacy identifier corresponding to a pharmacy, determining, by the one or more service provider computers, the pharmacy request file based at least upon a default pharmacy identifier.

5. The computer-implemented method of claim 4, wherein the pharmacy identifier is at least one of a National Provider ID (NPI), a National Council for Prescription Drug Programs (NCPDP) Provider ID, or an ePrescribing identifier.

6. The computer-implemented method of claim 1, further comprising:

determining, by the one or more service provider computers, whether the reversal request was approved, wherein if the reversal request transaction was not approved, re-submitting the reversal request transaction for a predetermined number of attempts.

7. The computer-implemented method of claim 1, further comprising:

determining a request type of the prescription benefit check request, wherein formatting the prescription request is based at least in part on the determined request type.

8. The computer-implemented method of claim 7, wherein the request type comprises a pharmacy request, a billing request, or a predetermination of benefits request.

9. The computer-implemented method of claim 8, wherein the pharmacy request comprises a pharmacy billing request.

10. The computer-implemented method of claim 1, further comprising:

determining, by the one or more service provider computers, a destination pharmacy claims processor computer corresponding to the prescription benefit check request, wherein the pharmacy claims processor computer comprises the destination pharmacy claims processor computer corresponding to the prescription benefit check request.

11. A system configured to determine and communicate benefit coverage information, the system comprising:

a database or data storage device configured to store one or more pharmacy request files comprising pharmacy information captured from a previously submitted pharmacy requests;

at least one memory operable to store computer-executable instructions; and at least one processor configured to access the at least one memory and execute the computer-executable instructions to:

receive, from a healthcare provider computer associated with a prescriber of a medication, a prescription benefit check request comprising at least one or more patient data identifying a patient, one or more patient pharmacy benefit data, an identifier for a prescribed medication, and one or more of prescriber data identifying the prescriber;

access the database or the data storage device and the one or more pharmacy request files stored therein comprising pharmacy information captured from one or more previously submitted pharmacy billing requests, the one or more pharmacy request files including at least a most frequently dispensed National Drug Code (NDC) number, a quantity dispensed associated with the preceding NDC Number, and a usual & customary charge;

determine a pharmacy request file corresponding to a patient pharmacy benefit data from the one or more pharmacy request files;

access the pharmacy request file to determine a most frequently dispensed NDC number, a quantity dispensed associated with the preceding NDC number, and a usual & customary charge corresponding to the identifier for the prescribed medication;

format a prescription request including at least the accessed most frequently dispensed NDC number, quantity dispensed associated with the preceding NDC number, and usual & customary charge corresponding to the identifier for the prescribed medication, the one or more patient data, and the one or more prescriber data included in the prescription benefit check request;

direct communication of the prescription request to a pharmacy claims processor computer for processing;

receive, from the pharmacy claims processor computer, a prescription response corresponding to the processed prescription request;

capture information from the prescription response;

generate a prescription benefit check response;

insert at least a portion of the information from the prescription response into the prescription benefit check response;

transmit the prescription benefit check response to the healthcare provider computer;

identify whether the prescription request is approved;

determine whether a predetermined time interval has elapsed since the prescription benefit check response was transmitted to the healthcare provider computer;

format a reversal request based at least in part upon a request type of the prescription benefit check request; and transmit the reversal request to the pharmacy claims processor computer.

12. The system of claim 11 wherein the at least one processor is further configured to access the at least one memory and execute the computer-executable instructions to determine a pharmacy claims processor computer to transmit the prescription request to, wherein the determination is based at least in part on one or more pharmacy claims processor computer identifiers submitted within the prescription benefit check request.

13. The system of claim 12, wherein the one or more pharmacy claims processor computer identifiers includes at least one of (i) a Banking Identification Number (BIN Number), (ii) the BIN Number and a Processor Control Number, or (iii) the BIN Number and a Group ID.

14. The system of claim 11, wherein the at least one processor is configured to access the at least one memory and execute the computer-executable instructions to determine a pharmacy request file corresponding to a patient pharmacy benefit data from the one or more pharmacy request files is further configured to:

determine whether the patient pharmacy benefit data includes a pharmacy identifier corresponding to a pharmacy, wherein:

if the patient pharmacy benefit data does include a pharmacy identifier corresponding to a pharmacy, determine the pharmacy request file based at least upon the pharmacy identifier, or if the patient pharmacy benefit data does not include a pharmacy identifier corresponding to a pharmacy, determine the pharmacy request file based at least upon a default pharmacy identifier.

15. The system of claim 14, wherein the pharmacy identifier is at least one of a National Provider ID (NPI), or a National Council for Prescription Drug Programs (NCPDP) Provider ID.

16. The system of claim 11, wherein the at least one processor is configured to access the at least one memory and execute the computer-executable instructions to:

determine whether the reversal request was approved, wherein if the reversal request transaction was not approved, re-submitting the reversal request transaction for a predetermined number of attempts.

17. The system of claim 11, wherein the at least one processor is configured to access the at least one memory and execute the computer-executable instructions to:

determine a request type of the prescription benefit check request, wherein formatting the prescription request is based at least in part on the determined request type.

18. The system of claim 17, wherein the request type comprises a pharmacy request, a billing request, or a pre-determination of benefits request.

19. The system of claim 18, wherein the pharmacy request comprises a pharmacy billing request.

20. The system of claim 11, wherein the at least one processor is configured to access the at least one memory and execute the computer-executable instructions to:

determine a destination pharmacy claims processor computer corresponding to the prescription benefit check request, wherein the pharmacy claims processor computer comprises the destination pharmacy claims processor computer corresponding to the prescription benefit check request.

* * * * *